United States Patent
Georges et al.

(10) Patent No.: US 8,080,552 B2
(45) Date of Patent: Dec. 20, 2011

(54) PYRIMIDYL DERIVATIVES AS PROTEIN KINASE INHIBITORS

(75) Inventors: Guy Georges, Habach (DE); Matthias Koerner, Grenzach-Wyhlen (DE); Irene Kolm, Penzberg (DE); Ulrike Reiff, Penzberg (DE); Wolfgang Schaefer, Mannheim (DE); Edgar Voss, Bichl (DE); Stefan Weigand, Penzberg (DE)

(73) Assignee: Hoffmann-LA Roche Inc., Nutley, NJ (US)

( * ) Notice: Subject to any disclaimer, the term of this patent is extended or adjusted under 35 U.S.C. 154(b) by 457 days.

(21) Appl. No.: 12/444,592

(22) PCT Filed: Dec. 19, 2007

(86) PCT No.: PCT/EP2007/011161
§ 371 (c)(1),
(2), (4) Date: Apr. 7, 2009

(87) PCT Pub. No.: WO2008/077548
PCT Pub. Date: Jul. 3, 2008

(65) Prior Publication Data
US 2010/0041684 A1  Feb. 18, 2010

(30) Foreign Application Priority Data
Dec. 22, 2006 (EP) .................... 06026650

(51) Int. Cl.
*A01N 43/54* (2006.01)
*C07D 239/42* (2006.01)
*C07D 401/04* (2006.01)
*A61K 31/505* (2006.01)
*C07D 239/02* (2006.01)
*C07D 239/00* (2006.01)

(52) U.S. Cl. ........ 514/256; 514/269; 544/319; 544/311; 544/242

(58) Field of Classification Search ............ 514/256, 514/269; 544/242, 311, 319
See application file for complete search history.

(56) References Cited

U.S. PATENT DOCUMENTS
2004/0053908 A1   3/2004   Funahashi et al.

FOREIGN PATENT DOCUMENTS
| WO | WO 02/32872 | 4/2002 |
|---|---|---|
| WO | WO2004/014870 | 2/2004 |
| WO | WO2005/051366 | 6/2005 |
| WO | WO2008/077548 | 7/2008 |

*Primary Examiner* — Sreeni Padmanabhan
*Assistant Examiner* — Samira Jean-Louis
(74) *Attorney, Agent, or Firm* — George W. Johnston; Patricia S. Rocha-Tramaloni; David E. Wildman

(57) ABSTRACT

Objects of the present invention are the compounds of formula (I), their pharmaceutically acceptable salts, enantiomeric forms, diastereoisomers and racemates, the preparation of the above compounds, medicaments containing them and their manufacture, as well as the use of the above compounds in the control or prevention of illnesses such as cancer.

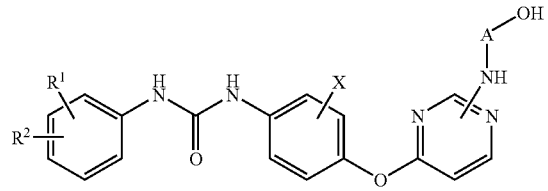

8 Claims, No Drawings

PYRIMIDYL DERIVATIVES AS PROTEIN KINASE INHIBITORS

The application claims the benefit of European Application No. 06026650.9, filed Dec. 22, 2006, which is hereby incorporated by reference in its entirety.

BACKGROUND OF THE INVENTION

The present invention relates to novel pyrimidyl derivatives, to a process for their manufacture, pharmaceutical compositions containing them and their manufacture as well as the use of these compounds as pharmaceutically active agents.

Protein kinases ("PKs") are enzymes that catalyze the phosphorylation of hydroxy groups on tyrosine, serine and threonine residues of proteins (Hunter, T., Cell 50 (1987) 823-829). The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger, J. and Ullrich, A., Neuron, 9 (1992) 383-391, which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epidermal growth factor receptor), HER2 (human epidermal growth factor receptor 2), HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily is referred to as the platelet derived growth factor receptor ("PDGFR") group, which includes PDGFR alpha, PDGFR beta, colony-stimulating factor 1 receptor (CSF-1R), c-kit and flt-3. These receptors consist of glycosylated extracellular domains composed of 5 immunoglobin-like loops and an intracellular domain wherein the tyrosine kinase domain is interrupted by a kinase inert domain.

Another group which, because of its similarity to the PDGFR subfamily, is sometimes subsumed into the latter group is the fetal liver kinase ("Flk") receptor subfamily. This group, containing extracellular immunoglobulin loops made up of kinase insert domain receptor/fetal liver kinase-1 (KDR/Flk-1), and fms-like tyrosine kinase 1 (Flt-1 and Flt-4). The human analogue of FLK-1 is the kinase insert domain-containing receptor KDR, which is also known as vascular endothelial cell growth factor receptor 2 or VEGFR-2, since it binds VEGF with high affinity.

Of the three PTK (protein tyrosine kinases) receptors for VEGFR identified VEGFR-1 (Flt-1); VEGRF-2 (Flk-1 or KDR) and VEGFR-3 (Flt-4), VEGFR-2 is of peculiar interest.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravasations of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and/or (vii) deposition of basement membrane and recruitment of perivascular cells to newly formed vessels.

Normal angiogenesis is activated during tissue growth, from embryonic development through maturity, and then enters a period of relative quiescence during adulthood.

Normal angiogenesis is also activated during wound healing, and at certain stages of the female reproductive cycle. Inappropriate or pathological angiogenesis has been associated with several disease states including various retinopathies; neuropathologic diseases like stroke, Alzheimer's disease and motor neuron disease, ischemic disease; atherosclerosis; chronic inflammatory disorders; rheumatoid arthritis, and cancer. The role of angiogenesis in disease states is discussed, for instance, in Fan, T. P., et al., Trends in Pharmacol Sci. 16 (1995) 57-66; Folkman, J., Nature Medicine 1 (1995) 27-31, and Greenberg, D. A., et al., Nature 438 (2005) 954-959.

It has been proposed that various receptor-type tyrosine kinases, and the growth factors binding to them, play a role in angiogenesis, although some may promote angiogenesis indirectly (Mustonen, T., et al., J. Cell Biol. 129 (1995) 895-898). One of these receptor-type tyrosine kinases is fetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs, R. B., et al., Oncogene 8 (1993) 11-15). VEGF and KDR are a ligand-receptor pair which plays a vital role in the proliferation of vascular endothelial cells and the formation and sprouting of blood vessels, referred to as vasculogenesis and angiogenesis respectively.

Angiogenesis is characterized by excessive activity of vascular endothelial growth factor (VEGF). VEGF actually consists of a family of ligands (Klagsbrun, M., et al., Cytokine & Growth Factor Reviews 7 (1996) 259-270). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumor growth has been shown to be susceptible to the antiangiogenic effects of VEGF receptor antagonists (Kim, K. J., et al., Nature 362 (1993) 841-844).

Solid turnouts can therefore be treated with tyrosine inhibitors since these tumors depend on angiogenesis for the formation of the blood vessels that are necessary to support their growth. These solid turnouts include monocytic leukaemia, carcinomas of the brain, urogenital tract, lymphatic system, stomach, larynx and lung, including lung adenocarcinoma and small cell lung carcinoma. Further examples include carcinomas in which overexpression or activation of Raf-activating oncogenes (for example, K-ras, erb-B) is observed. Such carcinomas include pancreatic and breast carcinoma. Inhibitors of these tyrosine kinases are therefore suitable for the prevention and treatment of proliferative diseases caused by these enzymes.

The angiogenic activity of VEGF is not limited to tumors. VEGF accounts for the angiogenic activity produced in several disease states including various retinopathies (e.g. in or near the retina in diabetic retinopathy), neuropathologic diseases like stroke, Alzheimer's disease and motor neuron disease, ischemic disease; atherosclerosis; chronic inflammatory disorders; rheumatoid arthritis, and cancer. The role of angiogenesis in disease states is discussed, for instance, in Fan, T. P., et al., Trends in Pharmacol Sci. 16 (1995) 57-66; Folkman, J., Nature Medicine 1 (1995) 27-31, and Greenberg, D. A., et al., Nature 438 (2005) 954-959.

A more complete listing of the known RTK subfamilies is described in Plowman, G. D., et al., Drugs News and Perspectives 7 (1994) 334-339, which is incorporated by reference, including any drawings, as if fully set forth herein.

In addition to the RTKs, there also exists a family of entirely intracellular PTKs called "non-receptor tyrosine kinases" or "cytoplasmic tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fak, Jak, LIMK and Ack) have been identified. The Src subfamily appear so far to be the largest group of CTKs and includes Src, Yes, Fyn, Lyn, Lck, Blk, Hck, Fgr, and Yrk. A further important group of CTKs is the Abl family including Abl and Arg. For a more detailed discussion of CTKs, see Bolen, J. B., Oncogene 8 (1993) 2025-2031, which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskeleton. The cytosol is the region within the cell where much of the cell's intermediary metabolic and biosynthetic activity occurs; e.g., it is in the cytosol that proteins are synthesized on ribosomes. The STKs include CDk2, Raf, the ZC family of kinases, the NEK family of kinases, and BUB 1.

The coordinated action of both protein kinases and phosphatases controls the levels of phosphorylation and, hence, the activity of specific target proteins. One of the predominant roles of protein phosphorylation is in signal transduction, where extracellular signals are amplified and propagated by a cascade of protein phosphorylation and dephosphorylation events, e.g. in the ras/raf pathway.

Activated Ras is necessary for the activation of the c-raf-1 proto-oncogene, but the biochemical steps through which Ras activates the Raf-1 protein (Ser/Thr) kinase are now well characterized. It has been shown that inhibiting the effect of active ras by inhibiting the rat kinase signaling pathway by administration of deactivating antibodies to raf kinase or by co-expression of dominant negative raf kinase or dominant negative MEK, the substrate of rat kinase, leads to the reversion of transformed cells to the normal growth phenotype see: Daum, G., et al., Trends Biochem. Sci. 19 (1994) 474-480; Fridman, M., et al., J. Biol. Chem. 269 (1994) 30105-30108. Kolch, W., et al., Nature 349 (1991) 426-428, and for review, Weinstein-Oppenheimer, C. R., et al., Pharm. & Therap. 88 (2000) 229-279.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, fibrosis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, trans-membrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have been made to identify small molecules which act as PK inhibitors.

WO 2002/032872 describes nitrogenous aromatic ring compounds useful as PK inhibitors. WO 2003/099771 and WO 2005/051366 relate to diaryl urea derivatives useful for the treatment of PK inhibitor dependent diseases.

SUMMARY OF THE INVENTION

The present invention relates to pyrimidyl derivatives of the general formula I,

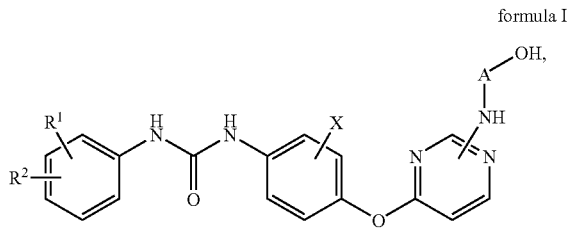

formula I wherein
R$^1$ is hydrogen, halogen, —CF$_3$, —OCF$_3$, alkyl, alkoxy, —Si(CH$_3$)$_3$, —C$_1$-C$_4$-alkylene-CN, —CN or —OCHF$_2$;
R$^2$ is hydrogen, halogen, —CF$_3$, —OCF$_3$, alkyl, alkoxy or —CN;
or alternatively R$^1$ and R$^2$ are adjacent and together with the carbon atom to which they are attached form a 5- or 6-membered heterocyclic ring, which is unsubstituted or substituted one to three times with halogen or alkyl;
X is hydrogen, fluorine or chlorine;

A is $C_1$-$C_6$-alkylene, which is unsubstituted or substituted once or twice by hydroxy;

and all pharmaceutically acceptable salts thereof

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as kinase inhibitors, especially as KDR kinase inhibitors or Raf kinase inhibitors, and may therefore be useful for the treatment of diseases mediated by said kinases.

KDR or Raf kinase inhibition exerts antiangiogenic and/or antiproliferative effect in tumor cell lines. This indicates that KDR and/or Raf kinase inhibitors may be useful in the treatment of i.e. hyperproliferative diseases such as cancer and in particular colorectal, breast, lung, prostate, pancreatic, gastric, bladder, ovarian, melanoma, neuroblastoma, cervical, kidney or renal cancers, leukemias or lymphomas.

KDR kinase is further known to be involved in a variety of other disease states. Compounds of the present invention may be further used as KDR kinase inhibitors, in the prevention and therapy of, for example, of diseases in which angiogenesis is part of the overall pathology, for example various retinopathies (e.g. in diabetic retinal vascularization), neuropathologic diseases like stroke, Alzheimer's disease and motor neuron disease, ischemic disease; atherosclerosis; chronic inflammatory disorders; rheumatoid arthritis, as well as various forms of cancer, since tumor growth is known to be dependent on angiogenesis (Fan, T. P., et al., Trends in Pharmacol Sci. 16 (1995) 57-66; Folkman, J., Nature Medicine 1 (1995) 27-31, and Greenberg, D. A., et al., Nature 438 (2005) 954-959, Weidner, N., et al., N. Engl. J. Med. 324 (1991) 1-8).

Objects of the present invention are the compounds of formula I and their tautomers, pharmaceutically acceptable salts, enantiomeric forms, diastereoisomers and racemates, their use as protein kinase inhibitors, in particular as KDR and/or Raf kinase inhibitors, the preparation of the above-mentioned compounds, medicaments or pharmaceutical compositions containing them and their manufacture as well as the use of the above-mentioned compounds in treatment, control or prevention of illnesses, especially of illnesses and disorders as mentioned above like tumors or cancer (e.g. colorectal, breast, lung, prostate, pancreatic, gastric, bladder, ovarian, melanoma, neuroblastoma, cervical, kidney or renal cancers, leukemias or lymphomas) or in the manufacture of corresponding medicaments or pharmaceutical compositions.

DETAILED DESCRIPTION OF THE INVENTION

1. Definitions

The term "alkyl" as used herein means a saturated, straight-chain or branched-chain hydrocarbon containing from 1 to 6 carbon atoms, preferably from 1 to 4 carbon atoms, such as methyl, ethyl, n-propyl, isopropyl, n-butyl, 2-butyl, t-butyl, n-pentyl, n-hexyl.

The term "alkoxy" as used herein means an alkyl-O— group wherein the alkyl is defined as above.

The term "halogen" as used herein means fluorine, chlorine, bromine or iodine, preferably fluorine, chlorine or bromine and more preferably fluorine or chlorine.

The term "$C_1$-$C_6$-alkylene" as used herein means a saturated, straight-chain or branched-chain, preferably straight-chain, hydrocarbon containing from 1 to 6 carbon atoms, preferably from 2 to 6 carbon atoms, and more preferably from 2 to 5 such as methylene, ethylene, trimethylene (1,3-propylene); tetramethylene (butylene), pentamethylene, methyl-methylene, ethyl-methylene, methyl-ethylene (1,2-propylene), 1,1-dimethyl-ethylene, 1,2-dimethyl-ethylene, ethyl-ethylene, n-propyl-ethylene, isopropyl-ethylene, tert-butyl-ethylene, 1-methyl-trimethylene, 2-methyl-trimethylene, 1-ethyl-trimethylene, 1-ethyl-trimethylene, 2-ethyl-trimethylene and the like, preferably ethylene, trimethylene; tetramethylene, methyl-ethylene, 1,1-dimethyl-ethylene, isopropyl-ethylene and tert-butyl-ethylene.

The term "$C_1$-$C_6$-alkylene, which is substituted once or twice by hydroxy" as used herein means $C_1$-$C_6$-alkylene as defined above which substituted once or twice by hydroxy, with the proviso that the hydroxy groups (including these one or two hydroxy and the hydroxy group of formula I) are not substituted at the same carbon atom. Examples of such $C_1$-$C_6$-alkylene, which is substituted once or twice by hydroxy are e.g. hydroxy-ethylene, hydroxy-trimethylene (1-hydroxy-1,3-propylene and 2-hydroxy-1,3-propylene), 1,2-dihydroxy-trimethylene, 1,2-dihydroxy-tetramethylene, 2,3-dihydroxy-tetramethylene hydroxymethyl-methylene, hydroxyethyl-methylene, hydroxymethyl-ethylene, 1-hydroxymethyl-2-methyl-ethylene, 1-hydroxy-2-hydroxymethyl-ethylene, 1-hydroxy-2-hydroxyethyl-ethylene, propyl-ethylene, 1-hydroxymethyl-trimethylene, 1,2-dihydroxymethyl-trimethylene, 1-hydroxy-2-hydroxymethyl-trimethylene, and the like, preferably hydroxymethyl-ethylene, 1-hydroxymethyl-2-methyl-ethylene.

The term "—$C_1$-$C_4$-alkylene" as used herein means alkylene as defined above, containing from 1 to 4 carbon atoms.

As used herein the term "5- or 6-membered heterocyclic ring" formed by $R^1$ and $R^2$ together with the carbon atoms to which they are attached, means a saturated or unsaturated cyclic hydrocarbon with 5 or 6 ring atoms of which 1 or 2 atoms are replaced by heteroatoms selected from S, N or O, preferably from N or O, and the remaining carbon-atoms, where possible, being unsubstituted or substituted one to three times with halogen, preferably fluorine, or alkyl. Examples of such "5- or 6-membered heterocyclic rings", formed by $R^1$ and $R^2$ include pyrrolidine, 3,3-dimethyl-pyrrolidine, [1,4]dioxane, [1,3]dioxolane or 2,2-difluoro-[1,3]dioxolane which form together with the phenyl moiety to which they are fused a 2,3-dihydro-1H-indole, 2,3-dihydro-1H-isoindole, 3,3-dimethyl-2,3-dihydro-1H-indole, 2,3-dihydro-benzo[1,4]dioxine, benzo[1,3]dioxole, or 2,2-difluoro-benzo[1,3]dioxole, preferably 3,3-dimethyl-2,3-dihydro-1H-indole and 2,2-difluoro-benzo[1,3]dioxole.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, in relation to mass spectrometry (MS) the term "ESI+" refers to positive electrospray ionization mode, the term "ESI-" refers to negative electrospray ionization mode, the term "AP+" refer to positive atmospheric pressure ionization mode and the term "AP-" refer to negative atmospheric pressure ionization mode.

2. Detailed Description $R^1$ is hydrogen, halogen, —$CF_3$, —$OCF_3$, alkyl, alkoxy, —$Si(CH_3)_3$, —$C_1$-$C_4$-alkylene-CN, —CN or —$OCHF_2$, preferably hydrogen, $CF_3$, —$OCF_3$, alkyl, —$Si(CH_3)_3$, or —$C_1$-$C_4$-alkylene-CN.

$R^2$ is hydrogen, halogen, —$CF_3$, —$OCF_3$, alkyl, alkoxy or —CN preferably hydrogen, halogen or alkoxy.

Or alternatively $R^1$ and $R^2$ are adjacent and together with the carbon atom to which they are attached form a 5- or 6-membered heterocycle ring, which is unsubstituted or substituted one to three times with halogen or alkyl, preferably a heterocyclic ring selected from 3,3-dimethyl-2,3-dihydro-1H-indole and 2,2-difluoro-benzo[1,3]dioxole.

X is hydrogen, fluorine or chlorine; preferably hydrogen or fluorine, more preferably hydrogen.

A is $C_1$-$C_6$-alkylene, which is unsubstituted or substituted once or twice, preferably once, by hydroxy; preferably the $C_1$-$C_6$-alkylene is unsubstituted by hydroxy.

Preferably the position of $R^1$ at the phenyl ring is meta to —NH—C(O)—NH-group.

Preferably the position of —NH-A-OH at the pyrimidine ring is meta to the —O-phenylene-group, which means that the 2- and 6-position are preferred (according to the numbering shown in the following partial structure).

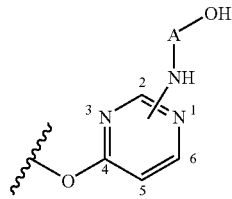

One embodiment of the invention are the compounds of formula I, wherein
$R^1$ is hydrogen, $CF_3$, —$OCF_3$, alkyl, —$Si(CH_3)_3$, or —$C_1$-$C_4$-alkylene-CN;
$R^2$ is hydrogen, halogen or alkoxy;

or alternatively $R^1$ and $R^2$ are adjacent and together with the carbon atom to which they are attached form a 5- or 6-membered heterocyclic ring, which is unsubstituted or substituted one to two times with fluorine or alkyl;
X is hydrogen, fluorine or chlorine;
A is $C_1$-$C_6$-alkylene, which is unsubstituted or substituted once or twice, preferably once, by hydroxy.

Such compounds, for example, may be selected from the group consisting of:
1-{4-[2-(3-Hydroxy-propylamino)-pyrimidin-4-yloxy]-phenyl}-3-(4-trifluoromethoxy-phenyl)-urea;
1-(4-tert-Butyl-phenyl)-3-{4-[2-(3-hydroxy-propylamino)-pyrimidin-4-yloxy]-phenyl}-urea;
1-(4-Chloro-phenyl)-3-{4-[2-(3-hydroxy-propylamino)-pyrimidin-4-yloxy]-phenyl}-urea;
1-{4-[2-(3-Hydroxy-propylamino)-pyrimidin-4-yloxy]-phenyl}-3-phenyl-urea;
1-{4-[2-(3-Hydroxy-propylamino)-pyrimidin-4-yloxy]-phenyl}-3-(4-trimethylsilanyl-phenyl)-urea;
1-[4-(Cyano-dimethyl-methyl)-phenyl]-3-{4-[2-(3-hydroxy-propylamino)-pyrimidin-4-yloxy]-phenyl}-urea;
1-[3-(Cyano-dimethyl-methyl)-phenyl]-3-{4-[2-(3-hydroxy-propylamino)-pyrimidin-4-yloxy]-phenyl}-urea; and
1-[3-(Cyano-methyl-methyl)-phenyl]-3-{4-[2-(3-hydroxy-propylamino)-pyrimidin-4-yloxy]-phenyl}-urea.

Another embodiment of the invention are the compounds of formula I-a,

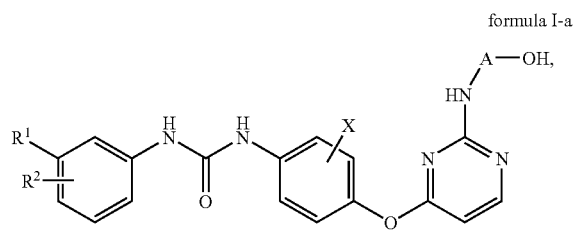

formula I-a wherein
$R^1$ is hydrogen, —$CF_3$, —$OCF_3$, alkyl, or —$C_1$-$C_4$-alkylene-CN;
$R^2$ is hydrogen, halogen or alkoxy;
or alternatively $R^1$ and $R^2$ are adjacent and together with the carbon atom to which they are attached form a 5- or 6-membered heterocyclic ring, which is unsubstituted or substituted one to two times with fluorine or alkyl;
X is hydrogen, fluorine or chlorine; and
A is $C_1$-$C_6$-alkylene, which is unsubstituted or substituted once or twice, preferably once, by hydroxy.

Another embodiment of the invention are the compounds of formula I-a, wherein
$R^1$ is hydrogen, $CF_3$, —$OCF_3$, alkyl, or —$C_1$-$C_4$-alkylene-CN; and
$R^2$ is hydrogen, halogen or alkoxy.

Another embodiment of the invention are the compounds of formula I-a, wherein
$R^1$ is hydrogen, $CF_3$, —$OCF_3$ or alkyl; and
$R^2$ is hydrogen, halogen or alkoxy.

Another embodiment of the invention are the compounds of formula I-a, wherein
$R^1$ is hydrogen, $CF_3$, —$OCF_3$ or alkyl;
$R^2$ is hydrogen, halogen or alkoxy; and
X is fluorine or chlorine.

Such compounds, for example, may be selected from the group consisting of:

1-{3-Chloro-4-[2-(3-hydroxy-propylamino)-pyrimidin-4-yloxy]-phenyl}-3-(4-chloro-3-trifluoromethyl-phenyl)-urea;

1-{2-Chloro-4-[2-(3-hydroxy-propylamino)-pyrimidin-4-yloxy]-phenyl}-3-(4-chloro-3-trifluoromethyl-phenyl)-urea;

1-(4-Chloro-3-trifluoromethyl-phenyl)-3-{3-fluoro-4-[2-(3-hydroxy-propylamino)-pyrimidin-4-yloxy]-phenyl}-urea; and 1-(4-Chloro-3-trifluoromethyl-phenyl)-3-{2-fluoro-4-[2-(3-hydroxy-propylamino)-pyrimidin-4-yloxy]-phenyl}-urea.

Another embodiment of the invention are the compounds of formula I-a, wherein
$R^1$ is hydrogen, $CF_3$, —$OCF_3$ or alkyl;
$R^2$ is hydrogen, halogen or alkoxy; and
X is hydrogen.

Another embodiment of the invention are the compounds of formula I-a, wherein
$R^1$ is —$CF_3$, —$OCF_3$ or alkyl;
$R^2$ is hydrogen, halogen or alkoxy;
X is hydrogen; and
A is $C_1$-$C_6$-alkylene, which is unsubstituted.

Such compounds, for example, may be selected from the group consisting of:

1-{4-[2-(3-Hydroxy-propylamino)-pyrimidin-4-yloxy]-phenyl}-3-(2-methoxy-5-trifluoromethyl-phenyl)-urea;

1-{4-[2-(3-Hydroxy-propylamino)-pyrimidin-4-yloxy]-phenyl}-3-(3-trifluoromethoxy-phenyl)-urea;

1-(3-tert-Butyl-phenyl)-3-{4-[2-(3-hydroxy-propylamino)-pyrimidin-4-yloxy]-phenyl}-urea;

1-{4-[2-(3-Hydroxy-propylamino)-pyrimidin-4-yloxy]-phenyl}-3-(3-trifluoromethyl-phenyl)-urea;

1-(2-Fluoro-5-trifluoromethyl-phenyl)-3-{4-[2-(3-hydroxy-propylamino)-pyrimidin-4-yloxy]-phenyl}-urea;

1-(4-Chloro-3-trifluoromethyl-phenyl)-3-{4-[2-(3-hydroxy-propylamino)-pyrimidin-4-yloxy]-phenyl}-urea;

1-(4-Chloro-3-trifluoromethyl-phenyl)-3-{4-[2-(4-hydroxy-butylamino)-pyrimidin-4-yloxy]-phenyl}-urea;

1-(4-Chloro-3-trifluoromethyl-phenyl)-3-{4-[2-(2-hydroxy-ethylamino)-pyrimidin-4-yloxy]-phenyl}-urea;

1-(4-Chloro-3-trifluoromethyl-phenyl)-3-{4-[2-(3-hydroxy-butylamino)-pyrimidin-4-yloxy]-phenyl}-urea;

1-(2-Chloro-5-trifluoromethyl-phenyl)-3-{4-[2-(3-hydroxy-propylamino)-pyrimidin-4-yloxy]-phenyl}-urea;

1-{4-[2-(2-Hydroxy-ethylamino)-pyrimidin-4-yloxy]-phenyl}-3-(3-trifluoromethyl-phenyl)-urea;

1-(4-Chloro-3-trifluoromethyl-phenyl)-3-{4-[2-((R)-2-hydroxy-1-methyl-ethylamino)-pyrimidin-4-yloxy]-phenyl}-urea;

1-(4-Chloro-3-trifluoromethyl-phenyl)-3-{4-[2-((R)-2-hydroxy-propylamino)-pyrimidin-4-yloxy]-phenyl}-urea;

1-(4-Chloro-3-trifluoromethyl-phenyl)-3-{4-[2-(2-hydroxy-1,1-dimethyl-ethylamino)-pyrimidin-4-yloxy]-phenyl}-urea;

1-(4-Chloro-3-trifluoromethyl-phenyl)-3-{4-[2-((S)-1-hydroxymethyl-2-methyl-propylamino)-pyrimidin-4-yloxy]-phenyl}-urea;

1-(4-Chloro-3-trifluoromethyl-phenyl)-3-{4-[2-((R)-1-hydroxymethyl-2,2-dimethyl-propylamino)-pyrimidin-4-yloxy]-phenyl}-urea;

1-(4-Chloro-3-trifluoromethyl-phenyl)-3-{4-[2-((S)-1-hydroxymethyl-2,2-dimethyl-propylamino)-pyrimidin-4-yloxy]-phenyl}-urea;

1-(4-Chloro-3-trifluoromethyl-phenyl)-3-{4-[2-((R)-1-hydroxymethyl-2-methyl-propylamino)-pyrimidin-4-yloxy]-phenyl}-urea;

1-(4-Chloro-3-trifluoromethyl-phenyl)-3-{4-[2-((S)-2-hydroxy-propylamino)-pyrimidin-4-yloxy]-phenyl}-urea; and 1-(4-Chloro-3-trifluoromethyl-phenyl)-3-{4-[2-((S)-2-hydroxy-1-methyl-ethylamino)-pyrimidin-4-yloxy]-phenyl}-urea.

Another embodiment of the invention are the compounds of formula I-a, wherein
$R^1$ is —$CF_3$, —$OCF_3$ or alkyl;
$R^2$ is hydrogen, halogen or alkoxy;
X is hydrogen; and
A is $C_1$-$C_6$-alkylene, which is substituted once or twice, preferably once, by hydroxy.

Such compounds, for example, may be selected from the group consisting of:

1-(4-Chloro-3-trifluoromethyl-phenyl)-3-{4-[2-(2-hydroxy-1-hydroxymethyl-ethylamino)-pyrimidin-4-yloxy]-phenyl}-urea;

1-(4-Chloro-3-trifluoromethyl-phenyl)-3-{4-[2-((1R,2R)-2-hydroxy-1-hydroxymethyl-propylamino)-pyrimidin-4-yloxy]-phenyl}-urea; and 1-(4-Chloro-3-trifluoromethyl-phenyl)-3-{4-[2-((1S,2S)-2-hydroxy-1-hydroxymethyl-propylamino)-pyrimidin-4-yloxy]-phenyl}-urea.

Another embodiment of the invention are the compounds of formula I-a, wherein
$R^1$ and $R^2$ are adjacent and together with the carbon atom to which they are attached form a 5- or 6-membered heterocyclic ring, which is unsubstituted or substituted one to two times with fluorine or alkyl;
X is hydrogen, fluorine or chlorine; and
A is $C_1$-$C_6$-alkylene, which is unsubstituted or substituted once or twice, preferably once, by hydroxy.

Another embodiment of the invention are the compounds of formula I-a, wherein
$R^1$ and $R^2$ are adjacent and together with the carbon atom to which they are attached form a 5- or 6-membered heterocyclic ring, which is unsubstituted or substituted one to two times with fluorine or alkyl;
X is hydrogen; and
A is $C_1$-$C_6$-alkylene, which is unsubstituted.

Such compounds, for example, may be selected from the group consisting of:

1-(2,2-Difluoro-benzo[1,3]dioxol-5-yl)-3-{4-[2-(3-hydroxy-propylamino)-pyrimidin-4-yloxy]-phenyl}-urea; and 1-(3,3-Dimethyl-2,3-dihydro-1H-indol-6-yl)-3-{4-[2-(3-hydroxy-propylamino)-pyrimidin-4-yloxy]-phenyl}-urea.

Another embodiment of the invention are the compounds of formula I-b, formula I-b

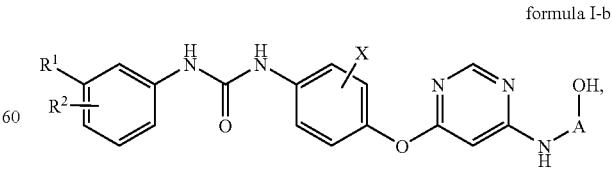

wherein
$R^1$ is hydrogen, —$CF_3$, —$OCF_3$, alkyl, or —$C_1$-$C_4$-alkylene-CN;
$R^2$ is hydrogen, halogen or alkoxy;

or alternatively R¹ and R² are adjacent and together with carbon atom to which they are attached form a 5- or 6-membered heterocyclic ring, which is unsubstituted or substituted one to two times with fluorine or alkyl, X is hydrogen, fluorine or chlorine; and A is $C_1$-$C_6$-alkylene, which is unsubstituted or substituted once or twice, preferably once, by hydroxy.

Another embodiment of the invention are the compounds of formula I-b, wherein

R¹ is —$CF_3$, —$OCF_3$ or alkyl; and

R² is hydrogen, halogen or alkoxy.

Another embodiment of the invention are the compounds of formula I-a, wherein

R¹ is —$CF_3$ or —$OCF_3$;

R² is hydrogen or halogen;

X is hydrogen; and

A is $C_1$-$C_6$-alkylene, which is unsubstituted.

Such compounds, for example, may be selected from the group consisting of:

1-{4-[6-(2-Hydroxy-ethylamino)-pyrimidin-4-yloxy]-phenyl}-3-(3-trifluoromethyl-phenyl)-urea;

1-{4-[6-(3-Hydroxy-propylamino)-pyrimidin-4-yloxy]-phenyl}-3-(3-trifluoromethyl-phenyl)-urea;

1-(4-Chloro-3-trifluoromethyl-phenyl)-3-{4-[6-(2-hydroxy-ethylamino)-pyrimidin-4-yloxy]-phenyl}-urea; and 1-(4-Chloro-3-trifluoromethyl-phenyl)-3-{4-[6-(3-hydroxy-propylamino)-pyrimidin-4-yloxy]-phenyl}-urea.

One embodiment of the invention is a process for the preparation of the compounds of formula I, by
reacting a compound of formula IV, formula IV

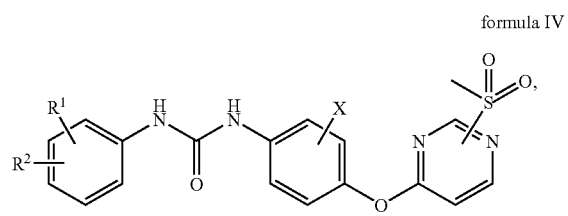

wherein R¹, R² and X have the significance given for formula I,
with a compound of formula IVa, formula IVa

wherein A has the significance given for formula I,
to give the compounds of formula I, formula I

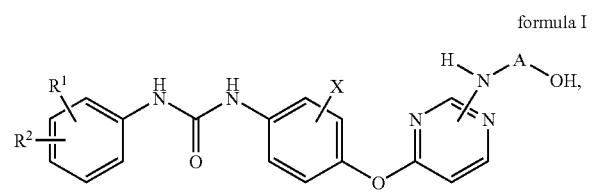

wherein R¹, R², X and A have the significance given for formula I.

The compounds of formula I, or a pharmaceutically acceptable salt thereof, which are subject of the present invention, may be prepared by any process known to be applicable to the preparation of chemically-related compounds. Such processes, when used to prepare a compound of the formula I, or a pharmaceutically-acceptable salt thereof, are illustrated by the following representative schemes 1 to 3 (and the examples) in which, unless otherwise stated, R¹, R², X and A have the significance given herein before for formula I. Necessary starting materials are either commercially available or they may be obtained by standard procedures of organic chemistry. The preparation of such starting materials is e.g. described within the accompanying examples or in the literature cited below with respect to scheme 1. Alternatively necessary starting materials are obtainable by analogous procedures to those illustrated which are within the ordinary skill of an organic chemist.

Scheme 1:

In scheme 1, a preferred method for the preparation of the compounds of formula I is described.

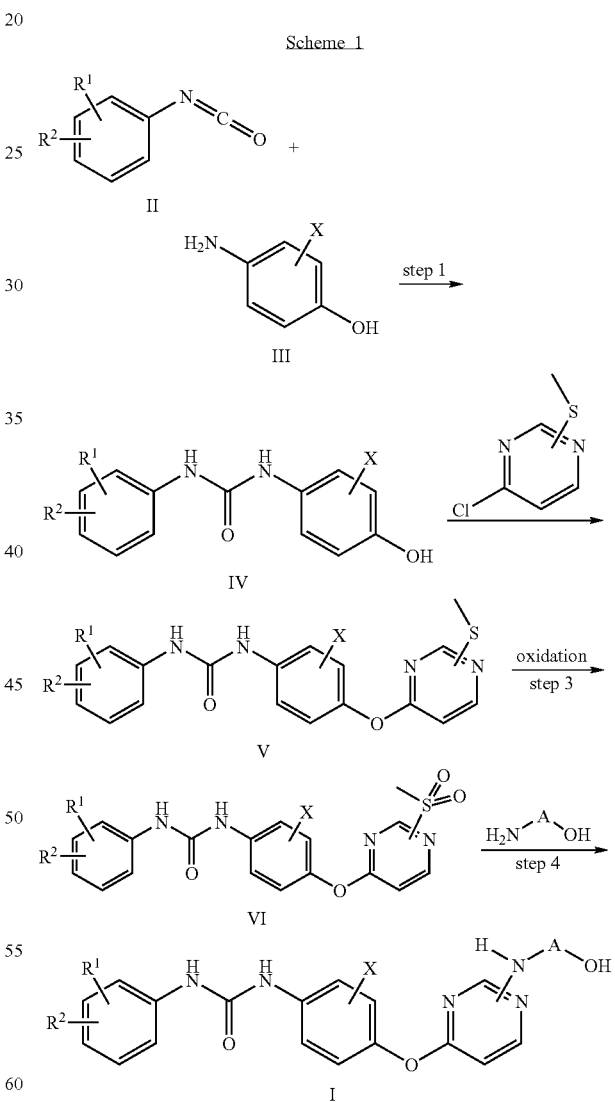

In scheme 1, R¹, R², X and A have the significance as given above for formula I.

Isocyanates II are reacted with aminophenols in conventional aprotic solvents, typically THF or dichloromethane to give phenol IV. The nucleophilic aromatic substitution of 4-chloro-2-methylsulfanyl-pyrimidine or 6-chloro-4-methylsulfanyl-pyrimidine with the phenolate salt of IV can be performed in dipolar aprotic solvents assisted by a suitable base. Appropriate reaction conditions include sodium hydride in dimethyl formamide or potassium/cesium carbonate in acetone or 2-butanone. The formed urea V can be oxidized to sulphone VI by methods known in the art. Typical reagents for this transformation are either organic peroxides like 3-chloro-peroxybenzoic acid or t-butyl hydroperoxide or inorganic peroxides like Oxone™, hydrogen peroxide. The most preferred oxidizing agent is 3-chloro-peroxybenzoic acid. To achieve the replacement of the sulphone moiety by appropriate amines (step 4), the components are mixed without or in a polar aprotic solvent such as dichloromethane, THF and stirred at room temperature or heated. If a solvent is used THF is most preferred one. Depending from the reactivity of the special amine one equivalent or an excess is used.

Scheme 2:

Scheme 2 shows an alternative route by to compounds of formula I by starting from the pyrimidine part.

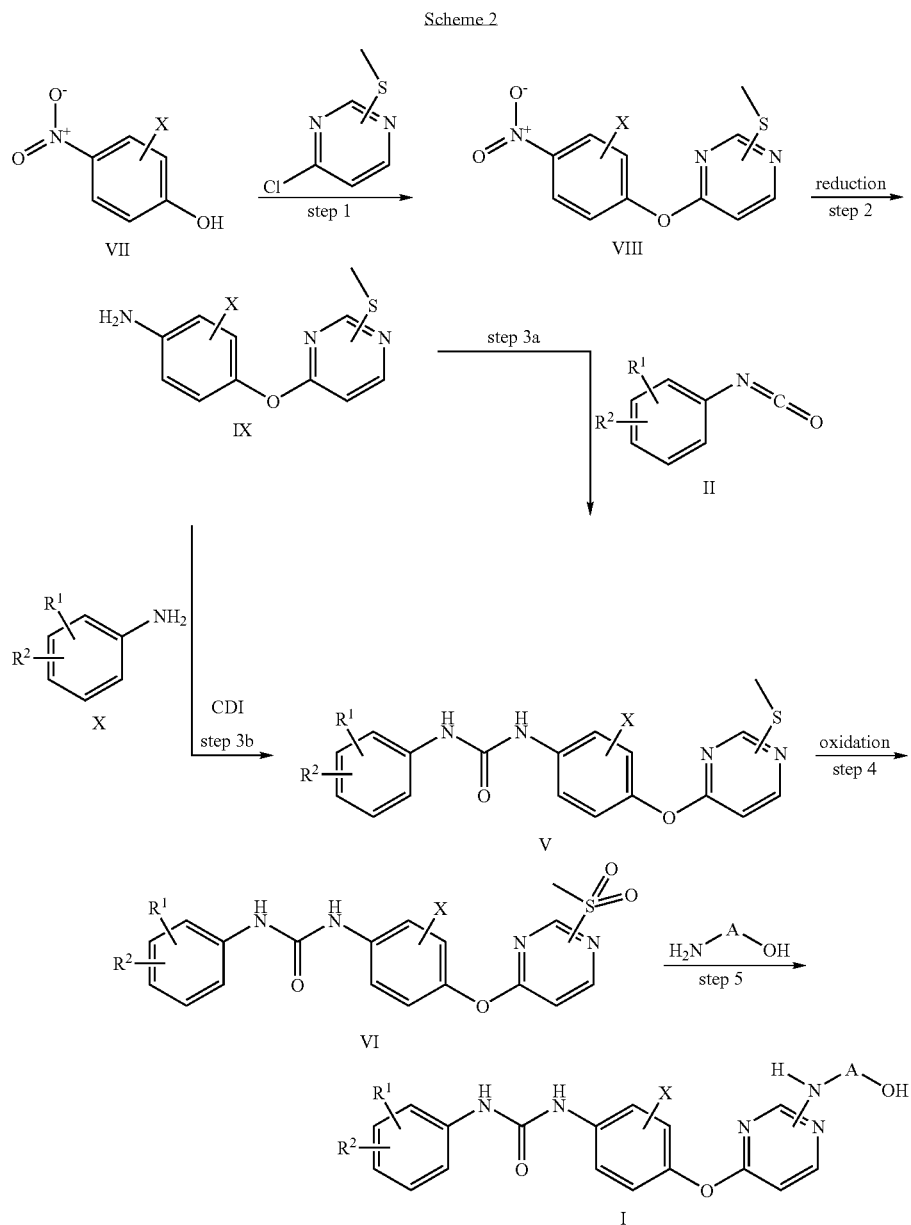

In scheme 2, $R^1$, $R^2$, X and A have the significance as given above for formula I.

Thus 4-chloro-2-methylsulfanyl-pyrimidine or 6-chloro-4-methylsulfanyl-pyrimidine is substituted with p-nitrophenols of general formula VII. This process is performed in the presence of a suitable base like sodium hydride in dimethylformamide or potassium carbonate or cesium carbonate in acetone or 2-butanone. In step 2 the obtained nitro compounds VII are reduced by well known reagents like complex metal hydrides in inert solvents, base metals such as iron or zinc under protic conditions or by hydrogenation. The preferred method is catalytic hydrogenation, more preferred hydrogenation over palladium on charcoal. Transformation of the obtained anilines IX to ureas V can be achieved by two different procedures, either as already described in scheme 1 by reaction with isocyanates of the general formula II or by use of carbonyldiimidazole (CDI) and anilines of the general formula X. The final steps to the desired compounds of formula I have already been described in scheme 1.

Scheme 3:

Scheme 3 describes an additional route to compounds of formula I by an early introduction of the pyrimidine side chain.

are for example t-butoxycarbonyl or derivatives thereof, which are removed by the addition of strong acids like trifluoroacetic acid (step 5).

The compounds of formula I can contain one or several chiral centers and can then be present in a racemic, a enantiomeric or diastereomeric form. The racemates can be separated according to known methods into the enantiomers. For instance, diastereomeric salts which can be separated by crystallization are formed from the racemic mixtures by reaction

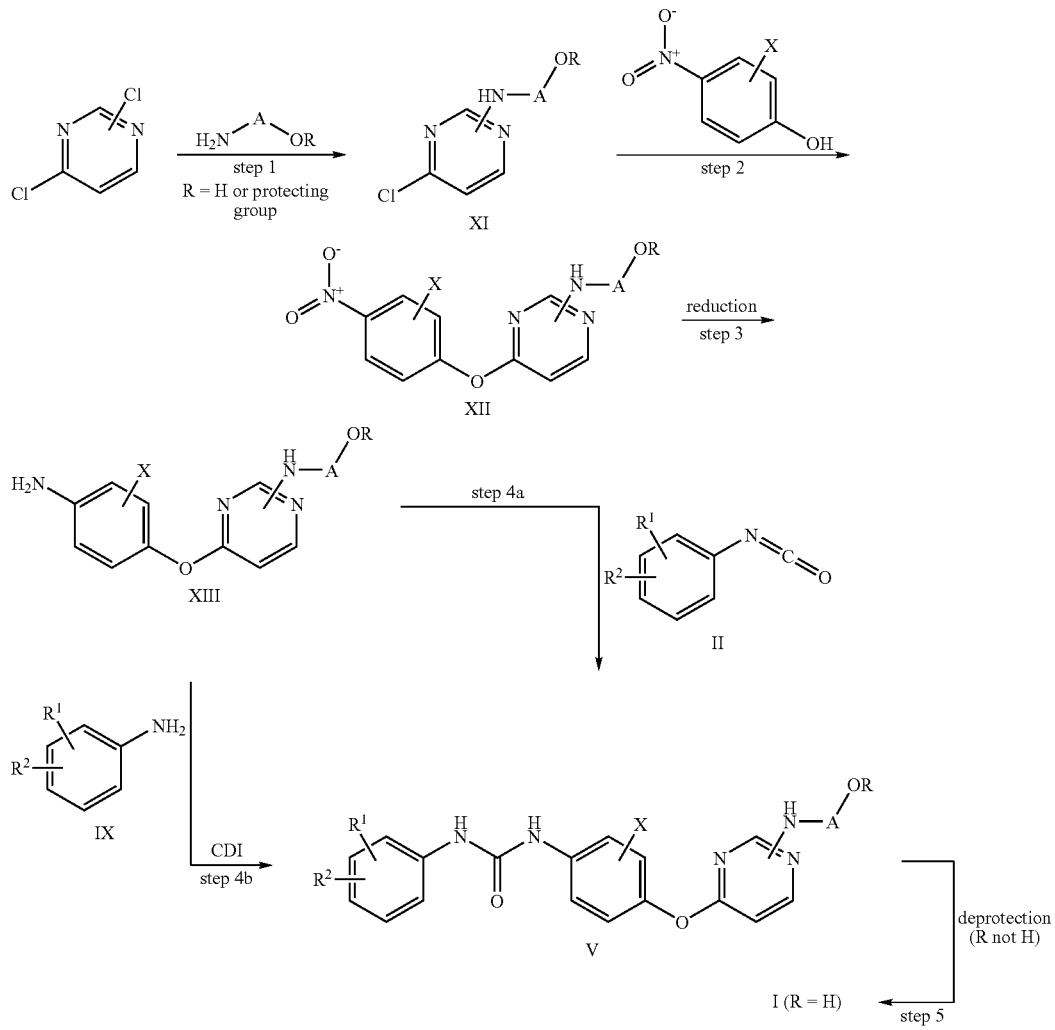

In scheme 1, $R^1$, $R^2$, X and A have the significance as given above for formula I and R is hydrogen or a hydroxy protection group.

Reaction of 2,4-dichloropyrimidine or 4,6-dichloropyrimidine with an aminoalcohol (either used in excess or in the presence of a base such as triethylamine) gives pyrimidines of formula XI. The reaction conditions for steps 2, 3, and 4 are similar to those explained in scheme 2 for the corresponding transformations. In case that R represents a protecting group an additional deprotecting step is required in order to obtain compounds I. Typical protecting groups are silyl protecting groups such as t-butyl-dimethylsilyl which are removed by addition of fluoride (step 5). Other suitable protecting groups with an optically active acid such as e.g. D- or L-camphorsulfonic acid. Alternatively separation of the enantiomers can also be achieved by using chromatography on chiral HPLC-phases which are commercially available.

Pharmaceutical composition or medicaments containing a compound of the present invention or a pharmaceutically acceptable salt thereof and a pharmaceutically acceptable carrier are an object of the present invention, as is a process for their production, which comprises bringing one or more compounds of the present invention and/or pharmaceutically acceptable salts and, if desired, one or more other therapeutically valuable substances into a galenical administration form together with one or more pharmaceutically acceptable carriers.

An embodiment of the invention is a pharmaceutical composition, containing one or more compounds according to formula I, together with pharmaceutically acceptable carriers.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a pharmaceutical composition, containing one or more compounds according to formula I, for the treatment of cancer.

Another embodiment of the invention is a pharmaceutical composition containing one or more compounds of formula I as active ingredients together with pharmaceutically acceptable carriers for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a pharmaceutical containing one or more compounds of formula I as active ingredients together with pharmaceutically acceptable carriers for the treatment of diseases in which angiogenesis is part of the overall pathology for example inflammation, diabetic retinal vascularization, as well as various forms of cancer.

Another embodiment of the invention is a pharmaceutical composition containing one or more compounds of formula I as active ingredients together with pharmaceutically acceptable carriers for the treatment of diseases mediated by an inappropriate activation of a KDR and/or Raf kinase.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of cancer.

Another embodiment of the invention is the use of a compound according to formula I, for the manufacture of corresponding pharmaceutical compositions for the treatment of diseases mediated by an inappropriate activation of KDR.

Another embodiment of the invention is the use of a compound according to formula I, for the manufacture of corresponding pharmaceutical compositions for the treatment of diseases mediated by an inappropriate activation of Raf kinase.

Another embodiment of the invention is the use of the compounds of formula I as KDR inhibitors.

Another embodiment of the invention is the use of the compounds of formula I as Raf kinase inhibitors.

Another embodiment of the invention is the use of the compounds of formula I as anti-angiogenic agents.

Another embodiment of the invention is the use of the compounds of formula I as anti-proliferating agents.

Another embodiment of the invention is the use of one or more compounds of formula I for the treatment of cancer.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic bases or, if the compounds of formula I contain a basic group in $R^1$, from organic or inorganic acids. Examples of base-addition salts include those derived from sodium, potassium, ammonium, quaternary ammonium hydroxides (such as for example, tetramethylammonium hydroxide), especially from sodium. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G. (editors), Handbook of Pharmaceutical Salts, Verlag Helvetica Chimica Acta (VHCA), Zürich (2002), or Bastin, R. J., et al., Organic Proc. Res. Dev. 4 (2000) 427-435.

Pharmacological Activity:

The compounds of formula I and their pharmaceutically acceptable salts possess valuable pharmacological properties. It has been found that said compounds show anti-proliferative and anti-angiogenic activity. Consequently the compounds of the present invention are useful in the therapy and/or prevention of proliferative diseases such as cancer. The activity of the present compounds as anti-proliferative agents is demonstrated by the following biological assay:

CellTiter-Glo™ Assay in HCT 116 Cells:

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl-247) were cultivated in RPMI 1640 medium with GlutaMAX™ I (Invitrogen, Cat-No. 61870-010), 5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (CellTiter-Glo™ Luminescent Cell Viability Assay, from Promega). In brief: the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st. Day:
  Medium: RPMI 1640 with GlutaMAX™ I (Invitrogen, Cat-Nr. 61870), 5% FCS (Sigma Cat.-No. F4135), Pen/Strep (Invitrogen, Cat No. 15140).
  HCT116 (ATCC-No. CCl-247): 1000 cells in 60 µl per well of 384 well plate (Greiner 781098, µClear-plate white)
  After seeding incubate plates 24 h at 37° C., 5% $CO_2$ 2nd. Day: Induction (Treatment with Compounds, 10 Concentrations):
  In order to achieve a final concentration of 30 µM as highest concentration 3.5 µl of 10 mM compound stock solution were added directly to 163 µl media. Then step e) of the dilution procedure described below, was followed.

In order to achieve the second highest to the lowest concentrations, a serial dilution with dilution steps of 1:3 was followed according to the procedure (a-e) as described here below:
a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1:47.6 (3.5 µl compound dilution to 163 µl media)
e) add 10 µl of every concentration to 60 µl media in the cell plate resulting in final concentration of DMSO: 0.3% in every well and resulting in 10 final concentration of compounds ranging from 30 µM to 0.0015 µM.
Each compound is tested in triplicate.
Incubate 120 h (5 days) at 37° C., 5% $CO_2$
Analysis:
  Add 30 µl CellTiter-Glo™ Reagent per well,
  shake 15 minutes at room temperature
  incubate further 45 minutes at room temperature without shaking
Measurement:
  Victor 2 scanning multiwell spectrophotometer (Wallac), Luminescence mode (0.5 sec/read, 477 nm)
  Determine IC50 using a non-linear curve fit (XLfit software (ID Business Solution Ltd., Guilford, Surrey, UK))

With all compounds a significant inhibition of HCT 116 cell viability was detected, which is exemplified by the compounds shown in Table 1.

TABLE 1

| Results: | |
|---|---|
| Examples | IC50 HCT 116 [µM] |
| 2 | 0.67 |
| 9 | 3.99 |
| 14 | 1.52 |
| 3, 4, 6, 7, 8, 10, 11, 12, 13, 17, 18, 20, 21, 22, 24, 25, 26, 28, 29 | 0.30-10.00 |

The activity of the present compounds as anti-angiogenic agents is demonstrated by the following biological assay:
CellTiter-Glo™ Assay in VEGF-Induced HUVEC Cells:
HUVEC-c (Human Umbilical Vein Endothelial Cells, from Promocell Cat-No. C-12200) cells were trypsinized, spinned down and plated in 384-well plates at 1500 cells per well in 60 µl endothelial basal medium (EBM-2 from Promocell, Cat-No. C-22211) with 0.5% Fetal Calf Serum (FCS, Sigma Cat-No. F4135 (FBS)). Cells were incubated overnight at 37° C., and the next day, test compounds (stock solution 140 µmol/l in medium with 4.2% dimethylsulfoxide (DMSO)) were added in 5 µl medium over a final concentration range of 10 µmol/l to 0.5 nmol/l and 0.3% DMSO. Compounds were tested in triplicates. After 2 hrs 5 µl VEGF (VEGF 165, R&D Systems, Cat-No. 293-VE-010, stock solution 280 ng/ml in medium) was added to a final concentration of 20 ng/ml. Cells were incubated for 72 hours at 37° C. in medium. Cell number was quantitated using CellTiter-Glo™ Luminescent Cell Viability Assay (from Promega) according to the instructions of the supplier. This assay measures the number of viable cells per well by measurement of luminescent signal based on amount of cellular ATP. IC50 are determined using a non-linear curve fit (XLfit software (ID Business Solution Ltd., Guilford, Surrey, UK)) (see also CellTiter-Glo™ assay in HCT 116 cells above).

With all compounds a significant inhibition of HUVEC cell viability was detected, which is exemplified by the compounds shown in Table 1.

TABLE 2

| Results: | |
|---|---|
| Examples | IC50 HCT 116 [µM] |
| 1 | 0.067 |
| 6 | 0.257 |
| 28 | 0.082 |
| 2, 3, 4, 5, 7, 8, 9, 10, 12, 13, 14, 15, 17, 18, 19, 20, 21, 22, 23, 25, 26, 29 | 0.005-0.750 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically acceptable, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:
a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.

4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The following examples are provided to aid the understanding of the present invention, the true scope of which is set forth in the appended claims. It is understood that modifications can be made in the procedures set forth without departing from the spirit of the invention.

EXPERIMENTAL PROCEDURES

Examples

Example 1

1-{4-[2-(3-Hydroxy-propylamino)-pyrimidin-4-yloxy]-phenyl}-3-(2-methoxy-5-trifluoromethyl-phenyl)-urea i) 3-(4-Chloro-pyrimidin-2-ylamino)-propan-1-ol A mixture of 99.8 g (0.670 mol) 2,4-dichloropyrimidine, 52.8 g (0.703 mol) 3-amino-propan-1-ol and 135.6 g (1.34 mol) triethylamine was stirred at room temperature for 12 h. The residue was treated with a mixture of 500 ml saturated sodium carbonate solution and 1000 ml ethyl acetate. The organic phase dried (sodium sulphate) and evaporated to give an oil that solidified in the refrigerator overnight. The material was extracted with 200 ml ethyl acetate and the soluble fraction containing the 2-isomer evaporated (the 4-isomer remains insoluble in ethyl acetate). Chromatography on silica (ethyl acetate) gave 28.9 g (23%) of 3-(4-Chloro-pyrimidin-2-ylamino)-propan-1-ol.

MS: 188.05 (ESI+)

$^1$H-NMR (400 Hz, [D$_6$], DMSO): δ=1.67 (quintet, 2H, CH$_2$—CH$_2$—CH$_2$), 3.30 (m, 2H, CH$_2$—NH 3.46 (q, 2H, CH$_2$—OH), 4.44 (t, 1H, OH), 6.63 (d, 1H, 5-H-pyrimidine), 7.59 (t, 1H, NH), 8.21 (br, 1H, 6-H-pyrimidine).

ii) 3-[4-(4-Nitro-phenoxy)-pyrimidin-2-ylamino]-propan-1-ol 1.37 g (54.3 mmol) sodium hydride was given to a solution of 7.19 g (51.7 mmol) 4-nitrophenol in 97 ml DMF. Stirring was continued for 30 min. at room temperature. 9.70 g (51.7 mmol) 3-(4-Chloro-pyrimidin-2-ylamino)-propan-1-ol was added and the mixture heated to 140° C. for 15 h. The reaction mixture was evaporated, taken up with water and extracted with dichloromethane. The organic phase was extracted with sodium carbonate solution, dried (sodium sulphate) and evaporated. The obtained yellow oil (11 g) was dissolved in 10 ml dichloromethane and purified by chromatography over silica (ethyl acetate) to give 8.66 g (58%) 3-[4-(4-Nitro-phenoxy)-pyrimidin-2-ylamino]-propan-1-ol

MS: 291.27 (ESI+), 289.2 (ESI−)

iii) 3-[4-(4-Amino-phenoxy)-pyrimidin-2-ylamino]-propan-1-ol

A solution of 8.66 g (29.8 mmol) 3-[4-(4-Nitro-phenoxy)-pyrimidin-2-ylamino]-propan-1-ol in a mixture of 173 ml THF and 173 ml methanol was hydrogenated over 3.46 g of 10% palladium on charcoal for 8 h. The catalyst was filtered off and the filtrate evaporated. The obtained oil was treated with a small amount of THF and the precipitate removed by filtration. Evaporation of the filtrate gave an oil that was purified by chromatography on silica (dichloromethane/ethanol 95:5) to give 5.77 g (74%) of 3-[4-(4-Amino-phenoxy)-pyrimidin-2-ylamino]-propan-1-ol as colorless oil.

MS: 261.12 (ESI+)

$^1$H-NMR (400 Hz, [D$_6$]DMSO): δ=1.61 (quintet, 2H, CH$_2$—CH$_2$—CH$_2$), 3.21 (br, 2H, CH$_2$—NH), 3.44 (q, 2H, CH$_2$—OH), 4.39 (br, 1H, OH), 5.00 (s, 2H, NH$_2$), 5.91 (br, 1H, 5-H-pyrimidine), 6.58 (2H, d, Ar—NH$_2$), 6.80 (d, 2H, Ar—NH$_2$), 6.98 (br, 1H, CH$_2$NH), 8.06 (br, d, 1H, 6-H-pyrimidine).

iv) 1-{4-[2-(3-Hydroxy-propylamino)-pyrimidin-4-yloxy]-phenyl}-3-(2-methoxy-5-trifluoromethyl-phenyl)-urea 205.6 mg (1.268 mmol) 1,1'-Carbonyl-diimidazol (CDI) were given to a solution of 220.3 mg (1.153 mmol) 2-methoxy-5-(trifluoromethyl)aniline in 4.0 ml dichloromethane. After stirring for 2 h a formed precipitate was dissolved by addition of 5 ml THF and the mixture stirred for 12 h at r.t. A solution of 300.0 mg (1.153 mmol) 3-[4-(4-Amino-phenoxy)-pyrimidin-2-ylamino]-propan-1-ol in 6 ml dichloromethane was added and the mixture stirred for 5 d at r.t. The reaction mixture was evaporated and the residue was purified by chromatography on silica gel (dichloromethane/methanol 95:5). The obtained material was washed with ether and dissolved in hot ethanol and evaporated. After treatment with a small amount of ethanol the precipitate was isolated by filtration and dried. Yield: 172 mg (31%) of the title compound.

MS: 478.41 (ESI+), 476.54 (ESI−)

$^1$H-NMR (400 Hz, [D$_6$]DMSO): δ=1.59 (quintet, 2H, CH$_2$—CH$_2$—CH$_2$), 3.21 (br, 2H, CH$_2$—NH), 3.39 (br, 2H, CH$_2$—OH), 3.98 (s, 3H, OCH$_3$), 4.37 (br, 1H, OH), 6.05 (br, 1H, 5-H-pyrimidine), 7.00 (br, 1H, CH$_2$NH), 7.10 (d, 2H, 3-H/5-H—Ar—NH), 7.21 (d, 1H, 3-H—ArCF$_3$), 7.32 (d, 1H, 4-H—ArCF$_3$), 7.49 (d, 2H, 2-H/6-H—Ar—NH), 8.12 (d, 1H, 6-H-pyrimidine), 8.49 (s, 1H, urea-NH), 8.55 (s, 1H, 6-H—ArCF$_3$), 8.49 (s, 1H, urea-NH).

Example 2

1-{4-[2-(3-Hydroxy-propylamino)-pyrimidin-4-yloxy]-phenyl}-3-(3-trifluoromethoxy-phenyl)-urea 149 mg (0.92 mmol) 1,1'-Carbonyl-diimidazol (CDI) were given to a solution of 148 mg (0.838 mmol) 3-trifluoromethoxyaniline in 4.0 ml dichloromethane and stirred for 12 h. A solution of 218 mg (0.838 mmol) 3-[4-(4-Amino-phenoxy)-pyrimidin-2-ylamino]-propan-1-ol in 6 ml dichloromethane was added and the mixture stirred for 12 h at r.t. The reaction mixture was evaporated and the residue was purified by chromatography on silica gel (dichloromethane/methanol 95:5). The obtained material was washed with dichloromethane, the precipitate was isolated by filtration and dried. Yield: 140 mg (36%) of the title compound.

MS: 464.47 (ESI+), 462.62 (ESI−).

$^1$H-NMR (400 Hz, [D$_6$]DMSO): δ=1.59 (quintet, 2H, CH$_2$—CH$_2$—CH$_2$), 3.22 (br, 2H, CH$_2$—NH), 3.40 (br, 2H, CH$_2$—OH), 4.37 (br, 1H, OH), 6.06 (br, 1H, 5-H-pyrimidine), 6.94 (d, 1H, ArOCF$_3$), 7.02 (br, 1H, CH$_2$NH), 7.10 (d, 2H, 3-H/5-H—Ar—NH), 7.30 (d, 1H, ArOCF$_3$), 7.40 (t, 1H, 5-H—ArOCF$_3$), 7.48 (d, 2H, 2-H/6-H—Ar—NH), 7.69 (s, 1H, 2-H—ArOCF$_3$), 8.12 (d, 1H, 6-H-pyrimidine), 8.81 (s, 1H, urea-NH), 9.00 (s, 1H, urea-NH).

Example 3

1-{4-[2-(3-Hydroxy-propylamino)-pyrimidin-4-yloxy]-phenyl}-3-(4-trifluoromethoxy-phenyl)-urea 180 mg (1.11 mmol) 1,1'-Carbonyl-diimidazol (CDI) were given to a solution of 179 mg (1.01 mmol) 3-trifluoromethoxyaniline in 4.0 ml dichloromethane and stirred for 12 h. A solution of 263 mg (1.01 mmol) 3-[4-(4-Amino-phenoxy)-pyrimidin-2-ylamino]-propan-1-ol in 6.0 ml dichloromethane was added within 30 min. and the mixture stirred for 12 h at r.t. The reaction mixture was filtered, the filtrate evaporated and the residue purified by chromatography on silica gel (dichloromethane/methanol 95:5). The obtained material was washed with dichloromethane, the precipitate was isolated by filtration and dried. Yield: 160 mg (34%) of the title compound.

MS: 464.47 (ESI+), 462.47 (ESI−).

$^1$H-NMR (400 Hz, [D$_6$]DMSO): δ=1.59 (quintet, 2H, CH$_2$—CH$_2$—CH$_2$), 3.22 (br, 2H, CH$_2$—NH), 3.38 (br, 2H, CH$_2$—OH), 4.37 (br, 1H, OH), 6.06 (br, 1H, 5-H-pyrimidine), 7.01 (br, 1H, CH$_2$NH), 7.11 (d, 2H, 3-H/5-H—Ar—NH), 7.28 (d, 2H, ArOCF$_3$), 7.48 (d, 2H, 2-H/6-H—Ar—NH), 7.56 (d, 2H, ArOCF$_3$), 8.12 (d, 1H, 6-H-pyrimidine), 8.76 (s, 1H, urea-NH), 8.87 (s, 1H, urea-NH).

Example 4

1-(3-tert-Butyl-phenyl)-3-{4-[2-(3-Hydroxy-propylamino)-pyrimidin-4-yloxy]-phenyl}-urea 172 mg (1.06 mmol) 1,1'-Carbonyl-diimidazol (CDI) were given to a solution of 144 mg (0.964 mmol) 3-t-butylaniline in 4.0 ml dichloromethane and stirred for 12 h. A solution of 263 mg (0.964 mmol) 3-[4-(4-Amino-phenoxy)-pyrimidin-2-ylamino]-propan-1-ol in 6.0 ml dichloromethane was added within 30 min. and the mixture stirred for 12 h at r.t. The reaction mixture was filtered, the filtrate evaporated and the residue purified by chromatography on silica gel (dichloromethane/methanol 95:5). The obtained material was washed with ether and the precipitate was isolated by filtration and dried. Yield: 170 mg (41%) of the title compound.

MS: 436.1 (ESI+), 434.07 (ESI−).

$^1$H-NMR (400 Hz, [D$_6$]DMSO): δ=1.26 (s, 9H, t-Bu), 1.59 (quintet, 2H, CH$_2$—CH$_2$—CH$_2$), 3.2 (br, 2H, CH$_2$—NH), 3.39 (br, 2H, CH$_2$—OH), 4.37 (br, 1H, OH), 6.04 (br, 1H, 5-H-pyrimidine), 7.00 (d, 1H, Ar-t-Bu), 7.04 (br, 1H, CH$_2$NH), 7.08 (d, 2H, 3-H/5-H—Ar—NH), 7.20 (t, 1H, 5-H—Ar-t-Bu), 7.29 (d, 1H, Ar-t-Bu), 7.46 (s, 1H, 2-H—Ar-t-Bu), 7.47 (d, 2H, 2-H/6-H—Ar—NH), 8.12 (d, 1H, 6-H-pyrimidine), 8.64 (s, 1H, urea-NH), 8.68 (s, 1H, urea-NH).

Example 5

1-(4-tert-Butyl-phenyl)-3-{4-[2-(3-Hydroxy-propylamino)-pyrimidin-4-yloxy]-phenyl}-urea A solution of 154 mg (0.880 mmol) 4-t-butyl-phenyl isocyanate in 3 ml THF was given at 0° C. to a solution of 229 mg (0.880 mmol) 3-[4-(4-Amino-phenoxy)-pyrimidin-2-ylamino]-propan-1-ol in 5 ml THF within 10 min. After stirring overnight the reaction mixture was evaporated and the residue purified by chromatography on silica gel (dichloromethane/methanol 97:3). The obtained material was washed with dichloromethane and the precipitate was isolated by filtration and dried. Yield: 80 mg (21%) of the title compound.

MS: 436.41 (ESI+), 434.35 (ESI−).

$^1$H-NMR (400 Hz, [D$_6$]DMSO): δ=1.26 (s, 9H, t-Bu), 1.59 (quintet, 2H, CH$_2$—CH$_2$—CH$_2$), 3.2 (br, 2H, CH$_2$—NH), 3.38 (br, 2H, CH$_2$—OH), 4.37 (br, 1H, OH), 6.05 (br, 1H, 5-H-pyrimidine), 7.03 (br, 1H, CH$_2$NH), 7.08 (d, 2H, 3-H/5-H—Ar—NH), 7.29 (d, 2H, Ar-t-Bu), 7.36 (d, 2H, Ar-t-Bu), 7.47 (d, 2H, 2-H/6-H—Ar—NH), 8.11 (d, 1H, 6-H-pyrimidine), 8.58 (s, 1H, urea-NH), 8.68 (s, 1H, urea-NH).

Example 6

1-(4-Chloro-phenyl)-3-{4-[2-(3-hydroxy-propylamino)-pyrimidin-4-yloxy]-phenyl}-urea A solution of 159 mg (1.033 mmol) 4-chlorophenyl isocyanate in 3 ml THF was given at 0° C. to a solution of 269 mg (1.033 mmol) 3-[4-(4-Amino-phenoxy)-pyrimidin-2-ylamino]-propan-1-ol in 5 ml THF within 10 min. After stirring overnight the reaction mixture was evaporated and the residue purified by chromatography on silica gel (ethyl acetate). The obtained material was recrystallized from 9 ml methanol to give 69 mg (16%) of the title compound.

MS: 414.3 (ESI+), 412.23 (ESI−).

$^1$H-NMR (400 Hz, [D$_6$]DMSO): δ=1.59 (quintet, 2H, CH$_2$—CH$_2$—CH$_2$), 3.2 (br, 2H, CH$_2$—NH), 3.39 (br, 2H, CH$_2$—OH), 4.37 (br, 1H, OH), 6.05 (br, 1H, 5-H-pyrimidine), 7.03 (br, 1H, CH$_2$NH), 7.10 (d, 2H, 3-H/5-H—Ar—NH), 7.33 (d, 2H, ArCl), 7.48 (m, 4H, 2-H/6-H—Ar—NH, ArCl), 8.12 (d, 1H, 6-H-pyrimidine), 8.78 (s, 1H, urea-NH), 8.85 (s, 1H, urea-NH).

Example 7

1-{4-[2-(3-Hydroxy-propylamino)-pyrimidin-4-yloxy]-phenyl}-3-(3-trifluoromethyl-phenyl)-urea A solution of 244 mg (1.306 mmol) 3-trifluoromethyl isocyanate in 3 ml THF was given at 0° C. to a solution of 229 mg (0.880 mmol) 3-[4-(4-Amino-phenoxy)-pyrimidin-2-ylamino]-propan-1-ol in 5 ml THF within 10 min. After stirring overnight the reaction mixture was evaporated and the residue purified by chromatography on silica gel (dichloromethane/methanol 95:5). The obtained material was washed with ether and the precipitate was isolated by filtration and dried. Yield: 170 mg (29%) of the title compound.

MS: 448.36 (ESI+), 446.30 (ESI−).

$^1$H-NMR (400 Hz, [D$_6$]DMSO): δ=1.59 (br, 2H, CH$_2$—CH$_2$—CH$_2$), 3.21 (br, 2H, CH$_2$—NH), 3.39 (br, 2H, CH$_2$—OH), 4.37 (br, 1H, OH), 6.05 (br, 1H, 5-H-pyrimidine), 7.01 (br, 1H, CH$_2$NH), 7.10 (d, 2H, 3-H/5-H—Ar—NH), 7.31 (d, 1H, 4-H—ArCF$_3$), 7.51 (d, 2H, 2-H/6-H—Ar—NH), 7.51 (t, 1H, 5-H—ArCF$_3$), 7.59 (d, 1H, 6-H—ArCF$_3$), 8.01 (s, 1H, 2-H—ArCF$_3$), 8.12 (d, 1H, 6-H-pyrimidine), 8.84 (s, 1H, urea-NH), 9.05 (s, 1H, urea-NH).

Example 8

1-(2-Fluoro-5-trifluoromethyl-phenyl)-3-{4-[2-(3-Hydroxy-propylamino)-pyrimidin-4-yloxy]-phenyl}-urea A solution of 233 mg (1.37 mmol) 2-fluoro-5-trifluoromethyl isocyanate in 3 ml THF was given at 0° C. to a solution of 296 mg (1.37 mmol) 3-[4-(4-Amino-phenoxy)-pyrimidin-2-ylamino]-propan-1-ol in 5 ml THF within 10 min. After stirring overnight the reaction mixture was evaporated and the residue purified by chromatography on silica gel (dichloromethane/methanol 95:5). The obtained material was washed with ether and the precipitate was isolated by filtration and dried. Yield: 150 mg (28%) of the title compound.

MS: 466.1 (ESI+), 464.01 (ESI−)

$^1$H-NMR (400 Hz, [D$_6$]DMSO): δ=1.59 (quintet, 2H, CH$_2$—CH$_2$—CH$_2$), 3.23 (br, 2H, CH$_2$—NH), 3.39 (br, 2H, CH$_2$—OH), 4.37 (br, 1H, OH), 6.07 (br, 1H, 5-H-pyrimidine), 7.03 (br, 1H, CH$_2$NH), 7.12 (d, 2H, 3-H/5-H—Ar—NH), 7.40 (m, 1H, ArCF$_3$), 7.50 (m, 3H, 2-H/6-H—Ar—NH, ArCF$_3$), 8.12 (d, 1H, 6-H-pyrimidine), 8.62 (d, 1H, 6-H—ArCF$_3$), 8.89 (s, 1H, urea-NH), 9.23 (s, 1H, urea-NH).

Example 9

1-(4-Chloro-3-trifluoromethylphenyl)-3-{4-[2-(3-Hydroxy-propylamino)-pyrimidin-4-yloxy]-phenyl}-urea A solution of 494 mg (2.23 mmol) 4-chloro-3-trifluoromethyl-phenyl isocyanate in 10 ml THF was added within 15 min. to a solution of 580 mg (2.23 mmol) 3-[4-(4-Amino-phenoxy)-pyrimidin-2-ylamino]-propan-1-ol in 10 ml THF and stirring continued overnight. The reaction mixture was evaporated and purified by HPLC/MS (Reprosil 100 C18, 10 µm, methanol/water 80:20) to give 500 mg oil that solidified by treatment with a small amount of ether. The precipitate was filtered and dried to yield 400 mg of the title compound.

MS: 482.19 (ESI+), 480.13 (ESI−).

$^1$H-NMR (400 Hz, [D$_6$]DMSO): δ=1.60 (quintet, 2H, CH$_2$—CH$_2$—CH$_2$), 3.22 (br, 2H, CH$_2$—NH), 3.39 (br, 2H, CH$_2$—OH), 4.35 (br, 1H, OH), 6.05 (br, 1H, 5-H-pyrimidine), 7.00 (br, 1H, CH$_2$NH), 7.10 (d, 2H, 3-H/5-H—Ar—NH), 7.49 (d, 2H, 2-H/6-H—Ar—NH), 7.60 (d, 1H, 5-H—ArCF$_3$), 7.65 (d, 1H, 6-H—ArCF$_3$), 8.10 (s, 1H, 2-H—ArCF$_3$), 8.12 (d, 1H, 6-H-pyrimidine), 8.87 (s, 1H, urea-NH), 9.14 (s, 1H, urea-NH).

Example 10

1-(4-Chloro-3-trifluoromethylphenyl)-3-{4-[2-(4-hydroxy-butylamino)-pyrimidin-4-yloxy]-phenyl}-urea i) 2-Methylsulfanyl-4-(4-nitrophenoxy)-pyrimidine 5.19 g 95% sodium hydride (205 mmol) were given at 0° C. to a solution of 25.98 g (187 mmol) p-nitrophenol and stirred for 30 min. 30.0 g 4-chloro-2-methylsulfanyl.pyrimidine were added and the mixture stirred for 4 h at 80° C. After stirring for 12 h at 70° C. the reaction mixture was poured into water (1000 ml) and the formed precipitate washed with water and dissolved in ethyl acetate. After extraction with 1 N HCl, the organic phase was dried (sodium sulphate) and evaporated. The residue was washed with ether and dried to give 17.3 g (94%) 2-methylsulfanyl-4-(4-nitrophenoxy)-pyrimidine.

MS: 264.17 (ESI+)

$^1$H-NMR (400 Hz, [D$_6$]DMSO): δ=2.35 (s, 3H, SCH$_3$), 6.95 (d, 1H, 5-H-pyrimidine), 7.56 (d, 2H, 2-H/6-H—ArNO$_2$), 8.34 (d, 2H, 3-H/5-H—ArNO$_2$), 8.59 (d, 1H, 6-H-pyrimidine).

ii) 4-(2-Methylsulfanyl-pyrimidin-4-yloxy)-phenylamine

A mixture of 120.0 g (456 mmol) 2-methylsulfanyl-4-(4-nitrophenoxy)-pyrimidine, 1200 ml ethanol, 1200 ml THF, and 24.0 g 10% palladium/C is hydrogenated at 46 mbar hydrogen pressure at r.t. for 8 h. The catalyst was removed by filtration, washed with 600 ml ethanol, then 300 ml THF and the combined filtrates evaporated. The residue was dissolved in a mixture of 700 ml ethyl acetate and 300 ml THF. The solution was dried over sodium sulphate and evaporated. The residue was stirred with 250 ml isohexane, the precipitate isolated and washed with 400 ml isohexane. Drying in vacuum at r.t. gave 102.5 g (96%) 4-(2-Methylsulfanyl-pyrimidin-4-yloxy)-phenylamine.

MS: 234.2 (ESI+)

$^1$H-NMR (400 Hz, [D$_6$]DMSO): δ=2.39 (s, 3H, SCH$_3$), 5.10 (s, 2H, NH$_2$), 6.58 (d, 1H, 5-H-pyrimidine), 6.60 (d, 2H, 2-H/6-H—ArNH$_2$), 6.85 (d, 2H, 3-H/5-H—ArNH$_2$), 8.42 (d, 1H, 6-H-pyrimidine).

iii) 1-(4-Chloro-3-trifluoromethyl-phenyl)-3-[4-(2-methylsulfanyl-pyrimidin-4-yloxy)-phenyl]-urea A solution of 4.81 g (21.7 mmol) 4-chloro-3-trifluoromethyl-phenyl isocyanate in 100 ml THF was added within 45 min. drop by drop at 0° C. to a solution of 5.06 g (21.7 mmol) 4-(2-methylsulfanyl-pyrimidin-4-yloxy)-phenylamine and stirring continued at r.t. overnight. The reaction mixture was evaporated and leached with 100 ml dichloromethane. The precipitate was isolated and dried to give 8.53 g (86%) 1-(4-Chloro-3-trifluoromethyl-phenyl)-3-[4-(2-methylsulfanyl-pyrimidin-4-yloxy)-phenyl]-urea.

MS: 455.47 (ESI+), 453.57 (ESI−).

$^1$H-NMR (400 Hz, [D$_6$]DMSO): δ=2.37 (s, 3H, SCH$_3$), 6.73 (d, 1H, 5-H-pyrimidine), 7.17 (d, 2H, 3-H/5-H—Ar—NH), 7.54 (d, 2H, 2-H/6-H—Ar—NH), 7.61 (d, 1H, 5-H—ArCF$_3$), 7.65 (s, 1H, 6-H—ArCF$_3$), 8.11 (s, 1H, 2-H—ArCF$_3$), 8.48 (d, 1H, 6-H-pyrimidine), 8.94 (s, 1H, urea-NH), 9.19 (s, 1H, urea-NH).

iv) 1-(4-Chloro-3-trifluoromethyl-phenyl)-3-[4-(2-methanesulfonyl-pyrimidin-4-yloxy)-phenyl]-urea 7.42 g (16.3 mmol) 1-(4-Chloro-3-trifluoromethyl-phenyl)-3-[4-(2-methylsulfanyl-pyrimidin-4-yloxy)-phenyl]-urea were dissolved in a mixture of 300 ml ethyl acetate and 150 ml dichloromethane. A solution of 5.92 g 77% 3-chloroperoxybenzoic acid in 80 ml dichloromethane was added drop by drop at −20° C. The reaction mixture was allowed to warm up to r.t. and stirred overnight. After extraction with 2 M sodium carbonate solution, the organic phase was dried (sodium sulphate) and evaporated. The residue was purified by chromatography on silica (ethyl acetate/n-heptane 2:1) to give 4.7 g (59%) 1-(4-Chloro-3-trifluoromethyl-phenyl)-3-[4-(2-methanesulfonyl-pyrimidin-4-yloxy)-phenyl]-urea as white amorphous solid.

MS: 487.19 (ESI+), 485.13 (ESI−).

$^1$H-NMR (400 Hz, [D$_6$]DMSO): δ=3.29 (s, 3H, SO$_2$CH$_3$), 7.25 (d, 2H, 3-H/5-H—Ar—NH), 7.34 (d, 1H, 5-H-pyrimidine), 7.58 (d, 2H, 2-H/6-H—Ar—NH), 7.61 (d, 1H, 5-H—ArCF$_3$), 7.66 (s, 1H, 6-H—ArCF$_3$), 8.11 (s, 1H, 2-H—ArCF$_3$), 8.89 (d, 1H, 6-H-pyrimidine), 9.00 (s, 1H, urea-NH), 9.23 (s, 1H, urea-NH).

v) 1-(4-Chloro-3-trifluoromethylphenyl)-3-{4-[2-(4-hydroxy-butylamino)-pyrimidin-4-yloxy]-phenyl}-urea A mixture of 216 mg (0.444 mmol) 1-(4-Chloro-3-trifluoromethyl-phenyl)-3-[4-(2-methanesulfonyl-pyrimidin-4-yloxy)-phenyl]-urea, 87.0 mg (0.976 mmol) 4-amino-butan-1-ol and 5 ml THF was stirred at r.t. for 12 h. The reaction mixture was evaporated and the residue purified by chromatography on silica (dichloromethane/ethanol 96:4). Yield 127 mg (58%) of the title compound.

MS: 496.34 (ESI+), 494.29 (ESI−).

$^1$H-NMR (400 Hz, [D$_6$]DMSO): δ=1.38, 1.45 (m, 4H, —CH$_2$—CH$_2$—CH$_2$OH), 3.18 (br, 2H, CH$_2$—NH), 3.37 (m, 2H,

CH$_2$—OH), 4.35 (t, 1H, OH), 6.05 (br, 1H, 5-H-pyrimidine), 7.1 (br, 1H, CH$_2$NH), 7.10 (d, 2H, 3-H/5-H—Ar—NH), 7.49 (d, 2H, 2-H/6-H—Ar—NH), 7.61 (d, 1H, 5-H—ArCF$_3$), 7.65 (d, 1H, 6-H—ArCF$_3$), 8.10 (s, 1H, 2-H—ArCF$_3$), 8.11 (br, 1H, 6-H-pyrimidine), 8.89 (s, 1H, urea-NH), 9.17 (s, 1H, urea-NH).

Example 11

1-(4-Chloro-3-trifluoromethylphenyl)-3-{4-[2-(2-hydroxy-ethylamino)-pyrimidin-4-yloxy]-phenyl}-urea A mixture of 144 mg (0.296 mmol) 1-(4-Chloro-3-trifluoromethyl-phenyl)-3-[4-(2-methanesulfonyl-pyrimidin-4-yloxy)-phenyl]-urea, 40 mg (0.65 mmol) 2-aminoethanol and 5 ml THF was stirred at r.t. for 12 h. The reaction mixture was evaporated and the residue purified by chromatography on silica (dichloromethane/ethanol 96:4). Yield 56 mg (40%) of the title compound.

MS: 468.36 (ESI+), 466.3 (ESI−).
$^1$H-NMR (400 Hz, [D$_6$]DMSO): δ=3.28 (br, 2H, CH$_2$—NH), 3.43 (m, 2H, CH$_2$—OH), 4.57 (t, 1H, OH), 6.08 (br, 1H, 5-H-pyrimidine), 6.95 (br, 1H, CH$_2$NH), 7.10 (d, 2H, 3-H/5-H—Ar—NH), 7.49 (d, 2H, 2-H/6-H—Ar—NH), 7.61 (d, 1H, 5-H—ArCF$_3$), 7.65 (d, 1H, 6-H—ArCF$_3$), 8.10 (s, 1H, 2-H—ArCF$_3$), 8.11 (d, 1H, 6-H-pyrimidine), 8.94 (s, 1H, urea-NH), 9.21 (s, 1H, urea-NH).

Example 12

1-(4-Chloro-3-trifluoromethylphenyl)-3-{4-[2-(3-hydroxy-butylamino)-pyrimidin-4-yloxy]-phenyl}-urea The compound was prepared from 1-(4-Chloro-3-trifluoromethyl-phenyl)-3-[4-(2-methanesulfonyl-pyrimidin-4-yloxy)-phenyl]-urea and 4-amino-butan-2-ol as described in example 10 for 4-amino-butan-1-ol instead.
$^1$H-NMR (400 Hz, [D$_6$]DMSO): δ=1.02 (br, 3H, CH$_3$), 1.49 (m, 2H, —CH$_2$—CHOH—), 3.22 (br, 2H, CH$_2$—NH), 3.6 (br, 1H, OH), 4.43 (m, 1H, CHOH), 6.06 (br, 1H, 5-H-pyrimidine), 7.0 (br, 1H, CH$_2$NH), 7.11 (d, 2H, 3-H/5-H—Ar—NH), 7.50 (d, 2H, 2-H/6-H—Ar—NH), 7.61 (d, 1H, 5-H—ArCF$_3$), 7.65 (d, 1H, 6-H—ArCF$_3$), 8.10 (s, 1H, 2-H—ArCF$_3$), 8.12 (br, 1H, 6-H-pyrimidine), 8.87 (s, 1H, urea-NH), 9.13 (s, 1H, urea-NH).

Example 13

1-{4-[2-(3-Hydroxy-propylamino)-pyrimidin-4-yloxy]-phenyl}-3-phenyl-urea 283 mg (1.75 mmol) 1,1'-Carbonyl-diimidazol (CDI) were given to a solution of 262 mg (1.59 mmol) 3-trimethylsilanyl-phenylamine (Kimes, A. S., J. Med. Chem. 35 (1992) 4683-4689) in 4.0 ml dichloro-methane and stirred for 12 h. A solution of 413 mg (1.59 mmol) 3-[4-(4-Amino-phenoxy)-pyrimidin-2-ylamino]-propan-1-ol in 6 ml dichloromethane was added within 30 min. and the mixture stirred for 12 h at r.t. The reaction mixture was evaporated and the residue was purified by chromatography on silica gel (dichloromethane/ethanol 96:4). The obtained material was washed with ether, the precipitate was isolated by filtration and dried.
Yield: 126 mg of the title compound.
MS: 380.15 (ESI+), 378.13 (ESI−).

$^1$H-NMR (400 Hz, [D$_6$]DMSO): δ=1.59 (br, 2H, CH$_2$—CH$_2$), 3.2 (br, 2H, CH$_2$—NH), 3.39 (br, 2H, CH$_2$—OH), 4.37 (br, 1H, OH), 6.05 (br, 1H, 5-H-pyrimidine), 6.97 (t, 1H, 4-H-Ph), 7.02 (br, 1H, CH$_2$NH), 7.09 (d, 2H, 3-H/5-H—Ar—NH), 7.28 (t, 2H, 3-H/5-H-Ph), 7.46 (t, 4H, 2-H/6-H-Ph, 2-H/6-H—Ar—NH), 8.12 (d, 1H, 6-H-pyrimidine), 8.67 (s, 1H, urea-NH), 8.72 (s, 1H, urea-NH).

Example 14

1-{4-[2-(3-Hydroxy-propylamino)-pyrimidin-4-yloxy]-phenyl}-3-(4-trimethylsilanyl-phenyl)-urea 187 mg (1.15 mmol) 1,1'-Carbonyl-diimidazol (CDI) were given to a solution of 182 mg (1.10 mmol) 4-trimethylsilanyl-phenylamine (Kimes, A. S., J. Med. Chem. 35, (1992) 4683-4689) in 4.0 ml dichloro-methane and stirred for 12 h. A solution of 286 mg (1.10 mmol) 3-[4-(4-Amino-phenoxy)-pyrimidin-2-ylamino]-propan-1-ol in 6 ml dichloromethane was added within 30 min. and the mixture stirred for 12 h at r.t. The reaction mixture was evaporated and the residue was purified by chromatography on silica gel (dichloromethane/methanol 95:5). The obtained material was washed with ether, the precipitate was isolated by filtration and dried. Yield: 90 mg of the title compound.
MS: 452.63 (ESI+).
$^1$H-NMR (400 Hz, [D$_6$]DMSO): δ=0.22 (s, 9H, CH$_3$), 1.59 (quintet, 2H, CH$_2$—CH$_2$—CH$_2$), 3.25 (br, 2H, CH$_2$—NH), 3.38 (br, 2H, CH$_2$—OH), 4.37 (br, 1H, OH), 6.05 (br, 1H, 5-H-pyrimidine), 7.03 (br, 1H, CH$_2$NH), 7.08 (d, 2H, 3-H/5-H—Ar—NH), 7.44 (m, 6H, Ar—Si, 2-H/6-H—Ar—NH), 8.13d, 1H, 6-H-pyrimidine), 8.74 (s, 1H, urea-NH), 8.76, 1H, urea-NH).

Example 15

1-(4-Chloro-3-trifluoromethyl-phenyl)-3-{3-chloro-4-[2-(3-hydroxy-propylamino)-pyrimidin-4-yloxy]-phenyl}-urea i) 3-[4-(2-Chloro-4-nitro-phenoxy)-pyrimidin-2-ylamino]-propan-1-ol
370 mg (14.7 mmol) sodium hydride was given to a solution of 2.31 g (13.3 mmol) 2-chloro-4-nitrophenol in 25 ml DMF. Stirring was continued for 30 min. at room temperature. 2.50 g (13.3 mmol) 3-(4-Chloro-pyrimidin-2-ylamino)-propan-1-ol were added and the mixture heated to 140° C. for 24 h. The reaction mixture was evaporated, taken up with water and extracted with dichloromethane. The organic phase was extracted with sodium carbonate solution, dried (sodium sulphate) and evaporated. The obtained material was dissolved in 3 ml dichloromethane and purified by chromatography over silica (dichloromethane/ethanol 95:5) to give 2.92 g (67%) 3-[4-(2-chloro-4-nitro-phenoxy)-pyrimidin-2-ylamino]-propan-1-ol.
MS: 325.37 (ESI+), 323.33 (ESI).
$^1$H-NMR (400 Hz, [D$_6$]DMSO): δ=1.60 (br, 2H, CH$_2$—CH$_2$—CH$_2$), 3.24 (br, 2H, CH$_2$—NH), 3.39 (br, 2H, CH$_2$—OH), 4.37 (br, 1H, OH), 6.34 (d, 1H, 5-H-pyrimidine), 7.09 (br, 1H, NH), 7.67 (d, 1H, 6-H—ArNO$_2$), 8.26 (d, 1H, 6-H-pyrimidine), 8.28 (d, 1H, 5-H—ArNO$_2$), 8.48 (s, 1H, 3-H—ArNO$_2$),
ii) 3-[4-(4-amino-2-chloro-phenoxy)-pyrimidin-2-ylamino]-propan-1-ol
A solution of 1.00 g (3.08 mmol) 3-[4-(2-chloro-4-nitro-phenoxy)-pyrimidin-2-ylamino]-propan-1-ol in a mixture of 30 ml ethyl acetate was hydrogenated over 200 mg palladium on barium sulphate for 10 h. The catalyst was filtered off and the filtrate evaporated. The obtained oil was dissolved in ethyl acetate and purified by chromatography on silica (ethyl acetate) to give 510 mg (56%) of 3-[4-(4-amino-2-chloro-phenoxy)-pyrimidin-2-ylamino]-propan-1-ol as colorless oil.

MS: 295.18 (ESI+)

$^1$H-NMR (400 Hz, [D$_6$]DMSO): δ=1.58 (m, 2H, CH$_2$—CH$_2$—CH$_2$), 3.22 (br, 2H, CH$_2$—NH), 3.38 (q, 2H, CH$_2$—OH), 4.37 (br, 1H, OH), 5.30 (s, 2H, NH$_2$), 6.02 (br, 1H, 5-H-pyrimidine), 6.53 (1H, d, 5-H—Ar—NH$_2$), 6.68 (s, 1H, 3-H—Ar—NH$_2$), 6.93 (d, 1H, 6-H—Ar—NH$_2$), 7.0 (br, 1H, CH$_2$NH), 8.10 (br, d, 1H, 6-H-pyrimidine).

iii) 1-(4-Chloro-3-trifluoromethyl-phenyl)-3-{3-chloro-4-[2-(3-hydroxy-propylamino)-pyrimidin-4-yloxy]-phenyl}-urea A solution of 205 mg (0.926 mmol) 4-chloro-3-trifluoromethyl-phenyl isocyanate in 3 ml THF was added within 10 min. to a solution of 273 mg (0.926 mmol) 3-[4-(4-amino-2-chloro-phenoxy)-pyrimidin-2-ylamino]-propan-1-ol in 3 ml THF and stirring continued overnight. The reaction mixture was evaporated and purified by chromatography on silica (dichloromethane/ethanol 97:3). The obtained material was stirred with dichloromethane. The precipitate was filtered and dried to yield 130 mg of the title compound.

MS: 515.87 (ESI+), 513.87 (ESI−).

$^1$H-NMR (400 Hz, [D$_6$]DMSO): δ=1.58 (br, 2H, CH$_2$—CH$_2$—CH$_2$), 3.25 (br, 2H, CH$_2$—NH), 3.35 (br, 2H, CH$_2$—OH), 4.35 (br, 1H, OH), 6.16 (br, 1H, 5-H-pyrimidine), 7.02 (br, 1H, CH$_2$NH), 7.26 (d, 1H, 5-H—Ar—NH), 7.37 (d, 1H, 6-H—Ar—NH), 7.62 (d, 1H, 5-H—ArCF$_3$), 7.67 (d, 1H, 6-H—ArCF$_3$), 7.79 (s, 1H, 2-H—Ar—NH), 8.10 (s, 1H, 2-H—ArCF$_3$), 8.16 (d, 1H, 6-H-pyrimidine), 9.08 (s, 1H, urea-NH), 9.26 (s, 1H, urea-NH).

Example 16

1-(4-Chloro-3-trifluoromethyl-phenyl)-3-{2-chloro-4-[2-(3-hydroxy-propylamino)-pyrimidin-4-yloxy]-phenyl}-urea i) 4-(3-Chloro-4-nitro-phenoxy)-2-methylsulfanyl-pyrimidine 160 mg (6.34 mmol) 95% sodium hydride was given to a solution of 1.00 g (5.76 mmol) 3-chloro-4-nitrophenol in 15 ml DMF. Stirring was continued for 30 min. at room temperature. 925 mg (5.76 mmol) 4-chloro-2-methylsulfanyl-pyrimidine was added and the mixture heated to 80° C. for 16 h. The reaction mixture was evaporated, taken up with water and extracted with ethyl acetate. The organic phase was extracted with water, dried (sodium sulphate) and evaporated. The obtained material was dissolved in ethyl acetate and purified by chromatography over silica (ethyl acetate/n-heptane) to give 1.10 g (64%) 4-(3-chloro-4-nitro-phenoxy)-2-methylsulfanyl-pyrimidine.

MS: 325.37 (ESI+), 323.33 (ESI−)

$^1$H-NMR (400 Hz, [D$_6$]DMSO): δ=2.37 (s, 3H, SCH$_3$), 6.96 (d, 1H, 5-H-pyrimidine), 7.54 (d, 1H, 6-H—ArNO$_2$), 7.87 (s, 1H, 2-H—ArNO$_2$), 8.21 (d, 1H, 5-H—ArNO$_2$), 8.59 (d, 1H, 6-H-pyrimidine).

ii) 2-Chloro-4-(2-methylsulfanyl-pyrimidin-4-yloxy)-phenylamine

A mixture of 1.10 g (3.69 mmol) 2-methylsulfanyl-4-(3-chloro-4-nitrophenoxy)-pyrimidine, 20 ml ethanol, 20 ml THF, and 300 mg palladium/BaSO$_4$ is hydrogenated at 50 mbar hydrogen pressure at r.t. for 8 h. The catalyst was removed by filtration, washed with 20 ml ethanol and evaporated. The residue was purified by chromatography on silica (ethyl acetate/isohexane 2:7) to give 320 mg (32%) 2-chloro-4-(2-methylsulfanyl-pyrimidin-4-yloxy)-phenylamine.

MS: 268.33 (ESI+)

$^1$H-NMR (400 Hz, [D$_6$]DMSO): δ=2.38 (s, 3H, SCH$_3$), 5.36 (s, 2H, NH$_2$), 6.66 (d, 1H, 5-H-pyrimidine), 6.83 (d, 1H, 6-H—ArNH$_2$), 6.92 (d, 1H, 5-H—ArNH$_2$), 7.15 (s, 1H, 3-H—ArNH$_2$), 8.45 (d, 1H, 6-H-pyrimidine).

iii) 1-(4-Chloro-3-trifluoromethyl-phenyl)-3-[2-chloro-4-(2-methylsulfanyl-pyrimidin-4-yloxy)-phenyl]-urea A solution of 281 mg (1.27 mmol) 4-chloro-3-trifluoromethyl-phenyl isocyanate in 3 ml THF was added within 5 min. drop by drop at 0° C. to a solution of 340 mg (1.27 mmol) 2-chloro-4-(2-methylsulfanyl-pyrimidin-4-yloxy)-phenylamine and stirring continued at r.t. overnight. The reaction mixture was evaporated and purified by chromatography on silica (ethyl acetate/isohexane 1:4) to give 162 mg (26%) 1-(4-chloro-3-trifluoromethyl-phenyl)-3-[2-chloro-4-(2-methylsulfanyl-pyrimidin-4-yloxy)-phenyl]-urea.

MS: 488.88 (ESI+).

$^1$H-NMR (400 Hz, [D$_6$]DMSO): δ=2.37 (s, 3H, SCH$_3$), 6.81 (d, 1H, 5-H-pyrimidine), 7.24 (d, 1H, 5-H—Ar—NH), 7.51 (s, 1H, 3-H—Ar—NH), 7.63 (m, 2H, 5-H/6-H—ArCF$_3$), 8.12 (d, 1H, 2-H—ArCF$_3$), 8.15 (d, 1H, 6-H—Ar—NH), 8.46 (s, 1H, urea-NH), 8.51 (d, 1H, 6-H-pyrimidine), 9.83 (s, 1H, urea-NH).

iv) 1-(4-Chloro-3-trifluoromethyl-phenyl)-3-[2-chloro-4-(2-methanesulfonyl-pyrimidin-4-yloxy)-phenyl]-urea 162 mg (0.331 mmol) 1-(4-Chloro-3-trifluoromethyl-phenyl)-3-[2-chloro-4-(2-methylsulfanyl-pyrimidin-4-yloxy)-phenyl]-urea were dissolved in a mixture of 4 ml ethyl acetate and 5 ml dichloromethane. A solution of 167 mg (0.745 mmol) 77% 3-chloro-peroxybenzoic acid in 10 ml dichloromethane/ethyl acetate 1:1 was added drop by drop at −20° C. The reaction mixture was allowed to warm up to r.t. and stirred overnight. After extraction with 2 M sodium carbonate solution, the organic phase was dried (sodium sulphate) and evaporated. The residue was purified by chromatography on silica (ethyl acetate) to give 71 mg (41%) 1-(4-Chloro-3-trifluoromethyl-phenyl)-3-[2-chloro-4-(2-methanesulfonyl-pyrimidin-4-yloxy)-phenyl]-urea.

MS: 520.92 (ESI+).

$^1$H-NMR (400 Hz, [D$_6$]DMSO): δ=3.29 (s, 3H, SO$_2$CH$_3$),), 7.33 (d, 1H, 5-H—Ar—NH), 7.43 (d, 1H, 5-H-pyrimidine), 7.63 (m, 2H, 5-H/6-H—ArCF$_3$), 7.89 (s, 1H, 3-H—Ar—NH), 8.12 (d, 1H, 2-H—ArCF$_3$), 8.20 (d, 1H, 6-H—Ar—NH), 8.51 (s, 1H, urea-NH), 8.92 (d, 1H, 6-H-pyrimidine), 9.87 (s, 1H, urea-NH).

v) 1-{2-Chloro-4-[2-(3-hydroxy-propylamino)-pyrimidin-4-yloxy]-phenyl}-3-(4-chloro-3-trifluoromethylphenyl)-urea A mixture of 71 mg (0.145 mmol) 1-(4-Chloro-3-trifluoromethyl-phenyl)-3-[2-chloro-4-(2-methanesulfonyl-pyrimidin-4-yloxy)-phenyl]-urea, 23 mg (0.30 mmol) 3-amino-propan-1-ol and 2 ml THF was stirred at r.t. for 12 h. The reaction mixture was evaporated and the residue purified by chromatography on silica (dichloromethane/ethanol 96:4). Yield 21 mg (28%) of the title compound.

MS: 515.97 (ESI+).

$^1$H-NMR (400 Hz, [D$_6$]DMSO): δ=1.59 (br, 4H, —CH$_2$—CH$_2$—CH$_2$OH), 3.2 (br, 2H, CH$_2$—NH), 3.38 (br, 2H, CH$_2$—OH), 4.37 (br, 1H, OH), 6.15 (br, 1H, 5-H-pyrimidine), 7.1 (br, 1H, CH$_2$NH), 7.17 (d, 1H, 5-H—Ar—NH), 7.41 (s, 1H, 3-H—Ar—NH), 7.63 (m, 2H, 5-H/6-H—ArCF$_3$), 8.08 (d, 1H, 6-H—Ar—NH), 8.11 (d, 1H, 2-H—ArCF$_3$), 8.15 (d, 1H, 6-H-pyrimidine), 8.45 (s, 1H, urea-NH), 9.81 (s, 1H, urea-NH).

Example 17

1-(4-Chloro-3-trifluoromethyl-phenyl)-3-{3-fluoro-4-[2-(3-hydroxy-propylamino)-pyrimidin-4-yloxy]-phenyl}-urea i) 3-[4-(2-Fluoro-4-nitro-phenoxy)-pyrimidin-2-ylamino]-propan-1-ol 358 mg (14.2 mmol) 95% sodium hydride was given to a solution of 2.12 g (13.5 mmol) 2-fluoro-4-nitrophenol in 25 ml DMF. Stirring was continued for 30 min. at room temperature. 2.53 g (13.5 mmol) 3-(4-Chloro-pyrimidin-2-ylamino)-propan-1-ol were added and the mixture heated to 140° C. for 24 h. The reaction mixture was evaporated, taken up with water and extracted with dichloromethane. The organic phase was extracted with sodium carbonate solution, dried (sodium sulphate) and evaporated. The obtained material was purified by chromatography over silica (dichloromethane/ethanol 95:5) to give 2.92 g (70%) 3-[4-(2-fluoro-4-nitro-phenoxy)-pyrimidin-2-ylamino]-propan-1-ol as slightly yellow oil.

MS: 309.26 (ESI+), 307.21 (ESI−).

$^1$H-NMR (400 Hz, [D$_6$]DMSO): δ=1.69 (m, 2H, CH$_2$—CH$_2$—CH$_2$), 3.47 (br, 2H, CH$_2$—NH), 3.59 (t, 2H, CH$_2$—OH), 5.11 (br, 1H, OH), 6.30 (d, 1H, 5-H-pyrimidine), 7.26 (s, 1H, NH), 7.39 (t, 1H, 6-H—ArNO$_2$), 8.08 (m, 2H, 3-H/5-H—ArNO$_2$), 8.20 (d, 1H, 6-H-pyrimidine).

ii) 3-[4-(4-amino-2-fluoro-phenoxy)-pyrimidin-2-ylamino]-propan-1-ol

A solution of 2.90 g (9.41 mmol) 3-[4-(2-fluoro-4-nitrophenoxy)-pyrimidin-2-ylamino]-propan-1-ol in a mixture of 50 ml TH/methanol 1:1 was hydrogenated over 500 mg 10% Pd/C for 10 h. The catalyst was filtered off and the filtrate evaporated. The obtained oil was dissolved in ethyl acetate and purified by chromatography on silica (dichloromethane/methanol 94:6) to give 1.70 g (65%) of 3-[4-(4-amino-2-fluoro-phenoxy)-pyrimidin-2-ylamino]-propan-1-ol.

MS: 279.27 (ESI+)

$^1$H-NMR (400 Hz, [D$_6$]DMSO): δ=1.58 (br, 2H, CH$_2$—CH$_2$—CH$_2$), 3.22 (br, 2H, CH$_2$—NH), 3.38 (br 2H, CH$_2$—OH), 4.37 (br, 1H, OH), 5.30 (s, 2H, NH$_2$), 6.07 (br, 1H, pyrimidine), 6.36 (1H, d, 5-H—Ar—NH$_2$), 6.44 (d, 1H, 3-H—Ar—NH$_2$), 6.91 (d, 1H, 6-H—Ar—NH$_2$), 6.98 (br, 1H, CH$_2$NH), 8.10 (br, d, 1H, pyrimidine).

iii) 1-(4-Chloro-3-trifluoromethyl-phenyl)-3-{3-fluoro-4-[2-(3-hydroxy-propylamino)-pyrimidin-4-yloxy]-phenyl}-urea A solution of 228 mg (1.03 mmol) 4-chloro-3-trifluoromethyl-phenyl isocyanate in 3 ml THF was added within 10 min. to a solution of 286 mg (1.03 mmol) 3-[4-(4-amino-2-fluoro-phenoxy)-pyrimidin-2-ylamino]-propan-1-ol in 5 ml THF and stirring continued overnight. The reaction mixture was evaporated and purified by chromatography on silica (dichloromethane/ethanol 97:3). The obtained material was stirred with dichloromethane. The precipitate was filtered and dried to yield 130 mg of the title compound.

MS: 500.41 (ESI+), 498.37 (ESI−).

$^1$H-NMR (400 Hz, [D$_6$]DMSO): δ=1.58 (br, 2H, CH$_2$—CH$_2$—CH$_2$), 3.2 (br, 2H, CH$_2$—NH), 3.3 (br, 2H, CH$_2$—OH), 4.36 (br, 1H, OH), 6.19 (br, 1H, 5-H-pyrimidine), 7.01 (br, 1H, CH$_2$NH), 7.23 (m, 2H, 5-H/6-H—Ar—NH), 7.64 (m 3H, 5-H/6-H—ArCF$_3$, 2-H—Ar—NH), 8.10 (s, 1H, 2-H—ArCF$_3$), 8.15 (br, 1H, 6-H-pyrimidine), 9.09 (s, 1H, urea-NH), 9.25 (s, 1H, urea-NH).

Example 18

1-(4-Chloro-3-trifluoromethyl-phenyl)-3-{2-fluoro-4-[2-(3-hydroxy-propylamino)-pyrimidin-4-yloxy]-phenyl}-urea i) 4-(3-Fluoro-4-nitro-phenoxy)-2-methylsulfanyl-pyrimidine 173 mg (6.85 mmol) 95% sodium hydride was given to a solution of 979 mg (6.23 mmol) 3-fluoro-4-nitrophenol in 10 ml DMF. Stirring was continued for 30 min. at room temperature. 1.00 g (6.23 mmol) 4-chloro-2-methylsulfanyl-pyrimidine was added and the mixture heated to 80° C. for 16 h. The reaction mixture was evaporated, taken up with water and extracted with ethyl acetate. The organic phase was extracted with water, dried (sodium sulphate) and evaporated. The obtained material was dissolved in ethyl acetate and purified by chromatography over silica (ethyl acetate/n-heptane 1:2) to give 570 mg 4-(3-fluoro-4-nitro-phenoxy)-2-methylsulfanyl-pyrimidine.

MS: 282.24 (ESI+).

$^1$H-NMR (400 Hz, [D$_6$]DMSO): δ=2.37 (s, 3H, SCH$_3$), 6.98 (d, 1H, 5-H-pyrimidine), 7.40 (d, 1H, 6-H—ArNO$_2$), 7.71 (d, 1H, 2-H—ArNO$_2$), 8.29 (d, 1H, 5-H—ArNO$_2$), 8.61 (d, 1H, 6-H-pyrimidine).

ii) 2-Fluoro-4-(2-methylsulfanyl-pyrimidin-4-yloxy)-phenylamine

A mixture of 570 mg (2.03 mmol) 2-methylsulfanyl-4-(3-fluoro-4-nitrophenoxy)-pyrimidine, 10 ml ethanol, 10 ml THF, and 200 mg 10% palladium/C is hydrogenated at 50 mbar hydrogen pressure at r.t. for 8 h. The catalyst was removed by filtration, washed with 10 ml ethanol and evaporated. The residue was purified by chromatography on silica (ethyl acetate/n-heptane 1:2) to give 200 mg (39%) 2-fluoro-4-(2-methylsulfanyl-pyrimidin-4-yloxy)-phenylamine.

MS: 252.16 (ESI+).

$^1$H-NMR (400 Hz, [D$_6$]DMSO): δ=2.38 (s, 3H, SCH$_3$), 5.14 (s, 2H, NH$_2$), 6.65 (d, 1H, 5-H-pyrimidine), 6.77 (d, 1H, 5-H—ArNH$_2$), 6.81 (t, 1H, 6-H—ArNH$_2$), 7.01 (d, 1H, 3-H—ArNH$_2$), 8.45 (d, 1H, 6-H-pyrimidine).

iii) 1-(4-Chloro-3-trifluoromethyl-phenyl)-3-[2-fluoro-4-(2-methylsulfanyl-pyrimidin-4-yloxy)-phenyl]-urea A solution of 162 mg (0.732 mmol) 4-chloro-3-trifluoromethyl-phenyl isocyanate in 3 ml THF was added within 5 min. drop by drop at 0° C. to a solution of 184 mg (0.732 mmol) 2-fluoro-4-(2-methylsulfanyl-pyrimidin-4-yloxy)-phenylamine and stirring continued at r.t. overnight. The reaction mixture was evaporated and treated with 10 ml ether. Isolation of the precipitate gave 140 mg (40%) 1-(4-chloro-3-trifluoromethyl-phenyl)-3-[2-fluoro-4-(2-methylsulfanyl-pyrimidin-4-yloxy)-phenyl]-urea.

MS: 473.35 (ESI+), 471.31 (ESI−).

$^1$H-NMR (400 Hz, [D$_6$]DMSO): δ=2.38 (s, 3H, SCH$_3$), 6.80 (d, 1H, 5-H-pyrimidine), 7.08 (d, 1H, 5-H—Ar—NH), 7.33 (s, 1H, 3-H—Ar—NH), 7.63 (m, 2H, 5-H/6-H—ArCF$_3$), 8.10 (t, 1H, 6-H—Ar—NH), 8.12 (s, 1H, 2-H—ArCF$_3$), 8.51 (d, 1H, 6-H-pyrimidine), 8.73 (s, 1H, urea-NH), 9.53 (s, 1H, urea-NH).

iv) 1-(4-Chloro-3-trifluoromethyl-phenyl)-3-[2-fluoro-4-(2-methanesulfonyl-pyrimidin-4-yloxy)-phenyl]-urea 133 mg (0.281 mmol) 1-(4-Chloro-3-trifluoromethyl-phenyl)-3-[2-fluoro-4-(2-methylsulfanyl-pyrimidin-4-yloxy)-phenyl]-urea were dissolved in a mixture of 4 ml ethyl acetate and 5 ml dichloromethane. A solution of 139 mg (0.619 mmol) 77% 3-chloro-peroxybenzoic acid in 10 ml dichloromethane/ethyl acetate 1:1 was added drop by drop at −20° C. The reaction mixture was allowed to warm up to r.t. and stirred overnight. After extraction with 2 M sodium carbonate solution, the organic phase was dried (sodium sulphate) and evaporated. Treatment of the residue with ethyl acetate and isolation of the precipitate gave 99 mg (70%) 1-(4-Chloro-3-trifluoromethyl-phenyl)-3-[2-fluoro-4-(2-methanesulfonyl-pyrimidin-4-yloxy)-phenyl]-urea.

MS: 505.44 (ESI+), 503.40 (ESI−).

v) 1-{2-Fluoro-4-[2-(3-hydroxy-propylamino)-pyrimidin-4-yloxy]-phenyl}-3-(4-chloro-3-trifluoromethylphenyl)-urea A mixture of 98 mg (0.194 mmol) 1-(4-Chloro-3-trifluoromethyl-phenyl)-3-[2-fluoro-4-(2-methanesulfonyl-pyrimidin-4-yloxy)-phenyl]-urea, 32 mg (0.43 mmol) 3-aminopropan-1-ol and 5 ml THF was stirred at r.t. for 12 h. The reaction mixture was evaporated and the residue purified by chromatography on silica (dichloromethane/ethanol 96:4). Yield 20 mg (21%) of the title compound.

MS: 500.42 (ESI+), 498.38 (ESI−).

$^1$H-NMR (400 Hz, [D$_6$]DMSO): δ=1.59 (br, 2H, —CH$_2$—CH$_2$—CH$_2$OH), 3.28 (br, 2H, CH$_2$—NH), 3.39 (br, 2H, CH$_2$—OH), 4.36 (br, 1H, OH), 6.13 (br, 1H, 5-H-pyrimidine), 7.01 (d, 1H, 5-H—Ar—NH), 7.05 (br, 1H, CH$_2$NH), 7.23 (d, 1H, 3-H—Ar—NH), 7.62 (s, 2H, 5-H/6-H—ArCF$_3$), 8.02 (m, 1H, 6-H—Ar—NH), 8.12 (d, 1H, 2-H—ArCF$_3$), 8.15 (d, 1H, 6-H-pyrimidine), 8.69 (s, 1H, urea-NH), 9.51 (s, 1H, urea-NH).

Example 19

1-(2-Chloro-5-trifluoromethyl-phenyl)-3-{4-[2-(3-hydroxy-propylamino)-pyrimidin-4-yloxy]-phenyl}-urea i) [4-(4-Amino-phenoxy)-pyrimidin-2-yl]-(3-trimethylsilanyloxy-propyl)-amine 1.99 ml (1.99 mmol) of 1M t-butyl-dimethylsilyl chloride in dichloromethane were added at 0° C. to a solution of 470 mg (1.81 mmol) 3-[4-(4-Amino-phenoxy)-pyrimidin-2-ylamino]-propan-1-ol and 256 mg (2.53 mmol) triethylamine in 5 ml dichloromethane. The reaction mixture was stirred for 12 h at r.t. and extracted with water. The organic phase was dried (sodium sulphate) and evaporated. The obtained material was purified by chromatography on silica (ethyl acetate/n-heptane 1:1) to give 520 mg (77%) oily [4-(4-Amino-phenoxy)-pyrimidin-2-yl]-(3-trimethylsilanyloxy-propyl)-amine.

MS: 375.28 (ESI+).

$^1$H-NMR (400 Hz, [D$_6$]DMSO): δ=0.00 (s, 6H, SiCH$_3$), 0.84 (s, 9H, CH$_3$), 1.64 (quintet, 2H, CH$_2$—CH$_2$—CH$_2$), 3.20 (br, 2H, CH$_2$—NH), 3.58 (t, 2H, CH$_2$—OSi), 4.99 (s, 2H, NH$_2$), 5.91 (br, 1H, pyrimidine), 6.55 (2H, d, Ar—NH$_2$), 6.77 (d, 2H, Ar—NH$_2$), 6.96 (br, 1H, CH$_2$NH), 8.05 (br, d, 1H, pyrimidine).

ii) 1-(2-Chloro-5-trifluoromethyl-phenyl)-3-{4-[2-(3-hydroxy-propylamino)-pyrimidin-4-yloxy]-phenyl}-urea 105 mg (0.65 mmol) 1,1'-Carbonyl-diimidazol (CDI) was given to a solution of 115 mg (0.59 mmol) 2-chloro-5-(trifluoromethyl)aniline in 4.0 ml dichloromethane. After stirring for 12 h at r.t. a solution of 220 mg (0.59 mmol) [4-(4-Amino-phenoxy)-pyrimidin-2-yl]-(3-trimethylsilanyloxy-propyl)-amine in 6 ml dichloromethane within 30 min. was added and the mixture stirred for 5 d at r.t. A solution of 1.4 ml (1.4 mmol) 1 M tetrabutylammonium fluoride in THF was given to the mixture and stirring continued for 12 h. The reaction mixture was evaporated and the residue was purified by chromatography on silica gel (dichloromethane/ethanol 96:4). Yield: 6 mg (2%) of the title compound.

MS: 482.43 (ESI+), 480.45 (ESI−)

$^1$H-NMR (400 Hz, [D$_6$]DMSO): δ=1.59 (quintet, 2H, CH$_2$—CH$_2$—CH$_2$), 3.21 (br, 2H, CH$_2$—NH), 3.38 (br, 2H, CH$_2$—OH), 4.37 (br, 1H, OH), 6.06 (br, 1H, 5-H-pyrimidine), 7.05 (br, 1H, CH$_2$NH), 7.12 (d, 2H, 3-H/5-H—Ar—NH), 7.37 (d, 1H, 3-H—ArCF$_3$), 7.51 (d, 2H, 2-H/6-H—Ar—NH), 7.72 (d, 1H, 4-H—ArCF$_3$), 8.13 (br, 1H, 6-H-pyrimidine), 8.62 (s, 1H, 6-H—ArCF$_3$), 8.64 (s, 1H, urea-NH), 9.62 (s, 1H, urea-NH).

Example 20

1-{4-[6-(2-Hydroxy-ethylamino)-pyrimidin-4-yloxy]-phenyl}-3-(3-trifluoromethyl-phenyl)-urea i) 4-Chloro-6-methylsulfanyl-pyrimidine To a solution of 4,6-dichloro-pyrimidine (10.0 g, 67 mmol) in THF (55 ml), sodium thiomethylate (5.175 g, 74 mmol) is added under inert gas atmosphere. The reaction mixture is stirred at 60° C. overnight. After cooling down to r.t., the reaction mixture is diluted with ethyl acetate and water (100 ml each). The organic phase is removed and the aqueous phase is extracted with ethyl actetate. The combined organic phases are washed and dried, and the solvent is evaporated to give 9.74 g (90%) of a pale yellow solid (contains ca. 9% of starting material and ca. 9% of 4,6-dimethylsulfanyl-pyrimidine) which is used without any further purification.

MS: 160.76 (AP+).

$^1$H-NMR (400 Hz, [D$_6$]DMSO): δ=2.57 (s, 3H, SCH$_3$), 7.68 (s, 1H, 5-H-pyrimidine), 8.79 (s, 1H, 2-H-pyrimidine).

ii) 4-Methylsulfanyl-6-(4-nitro-phenoxy)-pyrimidine

To a solution of 4-nitrophenol (8.04 g, 58 mmol) in DMF (36 ml) is added at 0° C. sodium hydride (2.5 g, 63 mmol, 60% in mineral oil) and stirring is continued for 30 minutes at r.t. A solution of 4-chloro-6-methylsulfanyl-pyrimidine (8.44 g, 52.5 mmol) in DMF (12 ml) is added and the reaction mixture is sealed in a reaction tube and heated in the microwave to 130° C. for 20 minutes. The reaction mixture is taken up in ethyl acetate and water. The organic phase is washed dried and evaporated. Recrystallization from ethyl acetate results in 6.08 g (44%) of an off-white powder of sufficient purity.

MS: 263.55 (AP+).

$^1$H-NMR (400 Hz, [D$_6$]DMSO): δ=2.58 (s, 3H, SCH$_3$), 7.20 (s, 1H, 5-H-pyrimidine), 7.51 (d, 2H, 2-H/6-H—ArNO$_2$), 8.33 (d, 2H, 3-H/5-H—ArNO$_2$), 8.59 (s, 1H, 2-H-pyrimidine).

iii) 4-(6-Methylsulfanyl-pyrimidin-4-yloxy)-phenylamine

A solution of 4-methylsulfanyl-6-(4-nitro-phenoxy)-pyrimidine (0.5 g, 1.9 mmol) in ethanol/THF (25 ml, 1:1) is added catalyst (10% Pd/C, 0.3 g, 0.28 mmol). The starting material is hydrogenated at 4 bar for 4 h at r.t. The catalyst is filtered off and the solvent is removed. Due to instability, the product is used without any further purification for the subsequent reaction.

MS: 233.73 (AP+).

$^1$H-NMR (400 Hz, [D$_6$]DMSO): δ=2.51 (s, 3H, SCH$_3$), 5.11 (s, 2H, NH$_2$), 6.59 (d, 2H, 2-H/6-H—ArNH$_2$), 6.78 (s, 1H, 5-H-pyrimidine), 6.83 (d, 2H, 3-H/5-H—ArNH$_2$), 8.51 (s, 1H, 2-H-pyrimidine).

iv) 1-[4-(6-Methylsulfanyl-pyrimidin-4-yloxy)-phenyl]-3-(3-trifluoromethyl-phenyl)-urea A solution of 4-(6-methylsulfanyl-pyrimidin-4-yloxy)-phenylamine (1.3 g, 5.5 mmol) in THF (24 ml) is cooled to 0° C. A solution of 3-(trifluoromethyl)phenyl isocyanate (790 µl, 5.5 mmol) in THF (24 ml) is added and stirring is continued overnight at r.t. The solvent is evaporated and the crude product is purified by silica gel chromatography using an ethyl acetate/heptane eluent (1:1) to give 1.76 g (75%) of a white powder.

MS: 420.73 (AP+), 418.78 (AP−).

$^1$H-NMR (400 Hz, [D$_6$]DMSO): δ=2.55 (s, 3H, SCH$_3$), 6.96 (s, 1H, 5-H-pyrimidine), 7.13 (d, 2H, 3-H/5-H—Ar—NH), 7.31 (d, 1H, 4-H—ArCF$_3$), 7.48-7.55 (m, 3H, 2-H/6-H—Ar—NH & 5-H—ArCF$_3$), 7.59 (d, 1H, 6-H—ArCF$_3$), 8.02 (s, 1H, 2-H—ArCF$_3$), 8.54 (s, 1H, 2-H-pyrimidine), 8.87 (s, 1H, urea-NH), 9.06 (s, 1H, urea-NH).

v) 1-[4-(6-Methanesulfonyl-pyrimidin-4-yloxy)-phenyl]-3-(3-trifluoromethyl-phenyl)-urea To a solution of 1-[4-(6-methylsulfanyl-pyrimidin-4-yloxy)-phenyl]-3-(3-trifluoromethyl-phenyl)-urea (1.66 g, 3.95 mmol) in DMF (33 ml) is added m-chloroperbenzoic acid (2.0 g, 11.8 mmol). The reaction mixture is stirred overnight at r.t., diluted with ethyl acetate (200 ml), washed, dried and evaporated to give 1.85 g (quantitative yield) of a white powder.

MS: 452.84 (AP+), 450.86 (AP−).

$^1$H-NMR (400 Hz, [D$_6$]DMSO): δ=3.36 (s, 3H, SO$_2$CH$_3$), 7.22 (d, 2H, 3-H/5-H—Ar—NH), 7.32 (d, 1H, 4-H—ArCF$_3$), 7.50-7.61 (m, 5H, 5-H—ArCF$_3$, 6-H—ArCF$_3$, 2-H/6-H—Ar—NH, 5-H-pyrimidine), 8.03 (s, 1H, 2-H—ArCF$_3$), 8.94 (s, 1H, urea-NH), 9.01 (s, 1H, 2-H-pyrimidine), 9.10 (s, 1H, urea-NH).

vi) 1-{4-[6-(2-Hydroxy-ethylamino)-pyrimidin-4-yloxy]-phenyl}-3-(3-trifluoromethyl-phenyl)-urea A solution of 1-[4-(6-methanesulfonyl-pyrimidin-4-yloxy)-phenyl]-3-(3-trifluoromethyl-phenyl)-urea (100 mg, 0.22 mmol) in dichloromethane (1 ml) and 2-aminoethanol (133 μl, 2.2 mmol) is sealed in a reaction tube and heated in the microwave at 110° C. for 15 minutes. The reaction mixture is evaporated and purified by preparative HPLC to yield 51 mg (53%) of a white powder.

MS: 433.89 (AP+), 431.99 (AP−).

$^1$H-NMR (400 Hz, [D$_6$]DMSO): δ=3.30 (m, 2H, CH$_2$—NH), 3.48 (m, 2H, CH$_2$—OH), 4.69 (br s, 1H, OH), 5.80 (s, 1H, 5-H-pyrimidine), 7.06 (d, 2H, 3-H/5-H—Ar—NH), 7.28-7.32 (m, 2H, 4-H—ArCF$_3$, NH-pyrimidine), 7.48-7.54 (m, 3H, 5-H—ArCF$_3$, 2-H/6-H—Ar—NH), 7.59 (d, 1H, 6-H—ArCF$_3$), 8.02 (s, 1H, 2-H-pyrimidine), 8.11 (d, 1H, 2-H—ArCF$_3$), 8.96 (s, 1H, urea-NH), 9.17 (s, 1H, urea-NH).

Example 21

1-{4-[6-(3-Hydroxy-propylamino)-pyrimidin-4-yloxy]-phenyl}-3-(3-trifluoromethyl-phenyl)-urea A solution of 1-[4-(6-methanesulfonyl-pyrimidin-4-yloxy)-phenyl]-3-(3-trifluoromethyl-phenyl)-urea (100 mg, 0.22 mmol) in dichloromethane (1 ml) and 2-aminopropanol (168 μl, 2.2 mmol) is sealed in a reaction tube and heated in the microwave at 110° C. for 15 minutes. The reaction mixture is evaporated and purified by preparative HPLC to yield 55 mg (55%) of a white powder.

MS: 447.99 (AP+), 445.95 (AP−).

$^1$H-NMR (400 Hz, [D$_6$]DMSO): δ=1.64 (m, 2H, middle CH$_2$), 3.30 (m, 2H, CH$_2$—NH), 3.44 (dt, 2H, CH$_2$—OH), 4.45 (t, 1H, OH), 5.74 (s, 1H, 5-H-pyrimidine), 7.07 (d, 2H, 3-H/5-H—Ar—NH), 7.27-7.32 (m, 2H, 4-H—ArCF$_3$, NH-pyrimidine), 7.48-7.54 (m, 3H, 5-H—ArCF$_3$, 2-H/6-H—Ar—NH), 7.59 (d, 1H, 6-H—ArCF$_3$), 8.01 (s, 1H, 2-H-pyrimidine), 8.11 (d, 1H, 2-H—ArCF$_3$), 8.88 (s, 1H, urea-NH), 9.08 (s, 1H, urea-NH).

Example 22

1-(4-Chloro-3-trifluoromethyl-phenyl)-3-{4-[6-(2-hydroxy-ethylamino)-pyrimidin-4-yloxy]-phenyl}-urea i) 1-(4-Chloro-3-trifluoromethyl-phenyl)-3-[4-(6-methylsulfanyl-pyrimidin-4-yloxy)-phenyl]-urea A solution of 4-(6-methylsulfanyl-pyrimidin-4-yloxy)-phenylamine (1.3 g, 5.5 mmol) in THF (24 ml) is cooled to 0° C. A solution of 4-chloro-3-(trifluoromethyl)phenyl isocyanate (1.22 g, 5.5 mmol) in THF (24 ml) is added dropwise and stirring is continued overnight at r.t. The solvent is evaporated and the crude product is purified by silica gel chromatography using an ethyl acetate/heptane eluent (1:1) to give 1.78 g (70%) of a white solid.

MS: 454.68 (AP+), 452.72 (AP−).

$^1$H-NMR (400 Hz, [D$_6$]DMSO): δ=2.54 (s, 3H, SCH$_3$), 7.00 (s, 1H, 5-H-pyrimidine), 7.19 (d, 2H, 3-H/5-H—Ar—NH), 7.52 (d, 2H, 2-H/6-H—Ar—NH), 7.60-7.67 (m, 2H, 5-H—ArCF$_3$ & 6-H—ArCF$_3$), 8.11 (s, 1H, 2-H—ArCF$_3$), 8.53 (s, 1H, 2-H-pyrimidine), 8.93 (s, 1H, urea-NH), 9.18 (s, 1H, urea-NH).

ii) 1-(4-Chloro-3-trifluoromethyl-phenyl)-3-[4-(6-methanesulfonyl-pyrimidin-4-yloxy)-phenyl]-urea To a solution of 1-(4-chloro-3-trifluoromethyl-phenyl)-3-[4-(6-methylsulfanyl-pyrimidin-4-yloxy)-phenyl]-urea (1.7 g, 3.74 mmol) in DMF (32 ml) is added m-chloroperbenzoic acid (1.94 g, 11.2 mmol). The reaction mixture is stirred overnight at r.t., diluted with ethyl acetate (200 ml), washed, dried and evaporated to give 1.93 g (quantitative yield) of a white powder.

MS: 486.78 (AP+), 484.84 (AP−).

$^1$H-NMR (400 Hz, [D$_6$]DMSO): δ=3.36 (s, 3H, SO$_2$CH$_3$), 7.23 (d, 2H, 3-H/5-H—Ar—NH), 7.56-7.68 (m, 5H, 5-H—ArCF$_3$, 6-H—ArCF$_3$, 2-H/6-H—Ar—NH, 5-H-pyrimidine), 8.12 (s, 1H, 2-H—ArCF$_3$), 8.98 (s, 1H, urea-NH), 9.00 (s, 1H, 2-H-pyrimidine), 9.21 (s, 1H, urea-NH).

iii) 1-(4-Chloro-3-trifluoromethyl-phenyl)-3-{4-[6-(2-hydroxy-ethylamino)-pyrimidin-4-yloxy]-phenyl}-urea A solution of 1-(4-chloro-3-trifluoromethyl-phenyl)-3-[4-(6-methanesulfonyl-pyrimidin-4-yloxy)-phenyl]-urea (100 mg, 0.2 mmol) in dichloromethane (1 ml) and 2-aminoethanol (124 μl, 2.0 mmol) is sealed in a reaction tube and heated in the microwave at 110° C. for 15 minutes. The reaction mixture is evaporated and purified by preparative HPLC to yield 50 mg (52%) of a white powder.

MS: 467.89 (AP+), 465.88 (AP−).

$^1$H-NMR (400 Hz, [D$_6$]DMSO): δ=3.30 (m, 2H, CH$_2$—NH), 3.48 (m, 2H, CH$_2$—OH), 4.69 (br s, 1H, OH), 5.80 (s, 1H, 5-H-pyrimidine), 7.06 (d, 2H, 3-H/5-H—Ar—NH), 7.31 (br s, 1H, NH-pyrimidine), 7.48 (d, 2H, 2-H/6-H—Ar—NH), 7.60-7.67 (m, 2H, 5-H—ArCF$_3$ & 6-H—ArCF$_3$), 8.11 (m, 2H, 2-H—ArCF$_3$ & 2-pyrimidine), 8.98 (s, 1H, urea-NH), 9.26 (s, 1H, urea-NH).

Example 23

1-(4-Chloro-3-trifluoromethyl-phenyl)-3-{4-[6-(3-hydroxy-propylamino)-pyrimidin-4-yloxy]-phenyl}-urea A solution of 1-(4-chloro-3-trifluoromethyl-phenyl)-3-[4-(6-methanesulfonyl-pyrimidin-4-yloxy)-phenyl]-urea (100 mg, 0.2 mmol) in dichloromethane (1 ml) and 2-aminopropanol (156 μL, 2.0 mmol) is sealed in a reaction tube and heated in the microwave at 110° C. for 15 minutes. The reaction mixture is evaporated and purified by preparative HPLC to yield 35 mg (36%) of a white powder.

MS: 481.93 (AP+).

$^1$H-NMR (400 Hz, [D$_6$]DMSO): δ=1.64 (m, 2H, middle CH$_2$), 3.30 (m, 2H, CH$_2$—NH), 3.48 (dt, 2H, CH$_2$—OH), 4.45 (br s, 1H, OH), 5.74 (s, 1H, 5-H-pyrimidine), 7.07 (d, 2H, 3-H/5-H—Ar—NH), 7.28 (t, 1H, NH-pyrimidine), 7.49 (d, 2H, 2-H/6-H—Ar—NH), 7.60-7.67 (m, 2H, 5-H—ArCF$_3$ & 6-H—ArCF$_3$), 8.11 (m, 2H, 2-H—ArCF$_3$ & 2-H-pyrimidine), 8.97 (s, 1H, urea-NH), 9.25 (s, 1H, urea-NH).

Example 24

1-[4-(Cyano-dimethyl-methyl)-phenyl]-3-{4-[2-(3-Hydroxy-propylamino)-pyrimidin-4-yloxy]-phenyl}-urea 188 mg (1.16 mmol) 1,1'-Carbonyl-diimidazol (CDI) were given to a solution of 175 mg (1.09 mmol) 4-(cyano-dimethyl-methyl)-phenylamine (Hicks, T. A., J. Med. Chem. 22 (1979) 1460-1464) in 4.0 ml dichloro-methane and stirred for 12 h. A solution of 284 mg (1.09 mmol) 3-[4-(4-Amino-phenoxy)-pyrimidin-2-ylamino]-propan-1-ol in 6 ml dichloromethane was added within 30 min. and the mixture stirred for 12 h at r.t. The reaction mixture was evaporated and the residue was purified by chromatography on silica gel (ethyl acetate). The obtained material was left overnight with dichloromethane, the precipitate filtered, washed with ether and dried. Yield: 180 mg (37%) of the title compound.

MS: 447.58 (ESI+).

$^1$H-NMR (400 Hz, [D$_6$]DMSO): δ=1.59 (br, 2H, CH$_2$—CH$_2$—CH$_2$), 1.67 (s, 6H, CH$_3$), 3.22 (br, 2H, CH$_2$—NH), 3.38 (br, 2H, CH$_2$—OH), 4.37 (br, 1H, OH), 6.05 (br, 1H, 5-H-pyrimidine), 7.05 (br, 1H, CH$_2$NH), 7.09 (d, 2H, 3-H/5-H—Ar—NH), 7.41 (d, 2H, Ar—C—CN), 7.49 (m, 4H, 2-H/6-H—Ar—NH, Ar—C—CN), 8.12 (d, 1H, 6-H-pyrimidine), 8.75 (s, 1H, urea-NH), 8.79 (s, 1H, urea-NH).

Example 25

1-[3-(Cyano-dimethyl-methyl)-phenyl]-3-{4-[2-(3-hydroxy-propylamino)-pyrimidin-4-yloxy]-phenyl}-urea 196 mg (1.21 mmol) 1,1'-Carbonyl-diimidazol (CDI) were given to a solution of 176 mg (1.10 mmol) 3-(cyano-dimethyl-methyl)-phenylamine in 4.0 ml dichloro-methane and stirred for 12 h. A solution of 286 mg (1.10 mmol) 3-[4-(4-Amino-phenoxy)-pyrimidin-2-ylamino]-propan-1-ol in 6 ml dichloromethane was added within 30 min. and the mixture stirred for 12 h at r.t. The reaction mixture was evaporated and the residue was purified by chromatography on silica gel (dichloromethane/ethanol 96:4). The obtained material was leached with ether, filtered and dried. Yield 74 mg (15%) of the title compound.

MS: 447.38 (ESI+), 445.32 (ESI−).

$^1$H-NMR (400 Hz, [D$_6$]DMSO): δ=1.59 (br, 2H, CH$_2$—CH$_2$—CH$_2$), 1.68 (s, 6H, CH$_3$), 3.2 (br, 2H, CH$_2$—NH), 3.39 (br, 2H, CH$_2$—OH), 4.38 (br, 1H, OH), 6.06 (br, 1H, 5-H-pyrimidine), 7.05 (br, 1H, CH$_2$NH), 7.10 (m, 3H, 3-H/5-H—Ar—NH, 4-H—Ar—C—CN), 7.34 (t, 1H, 5-H—Ar—C—CN), 7.42 (d, 1H, 6-H—Ar—C—CN), 7.48 (d, 2H, 2-H/6-H—Ar—NH), 7.66 (s, 1H, 2-H—Ar—C—CN), 8.12 (d, 1H, 6-H-pyrimidine), 8.72 (s, 1H, urea-NH), 8.84 (s, 1H, urea-NH).

Example 26

1-[3-(Cyano-methyl-methyl)-phenyl]-3-{4-[2-(3-hydroxy-propylamino)-pyrimidin-4-yloxy]-phenyl}-urea 222 mg (1.37 mmol) 1,1'-Carbonyl-diimidazol (CDI) were given to a solution of 182 mg (1.24 mmol) 2-(3-amino-phenyl)-propionitrile in 4.0 ml dichloro-methane and stirred for 12 h. A solution of 324 mg (1.24 mmol) 3-[4-(4-Amino-phenoxy)-pyrimidin-2-ylamino]-propan-1-ol in 6 ml dichloromethane was added within 30 min. and the mixture stirred for 12 h at r.t. The reaction mixture was evaporated and the residue was purified by chromatography on silica gel (dichloromethane/ethanol 96:4). The obtained material was leached with ether, filtered and dried. Yield 200 mg (37%) of the title compound.

MS: 433.21 (ESI+), 431.15 (ESI−).

$^1$H-NMR (400 Hz, [D$_6$]DMSO): δ=1.54 (d, 3H, CH$_3$), 1.59 (br, 2H, CH$_2$—CH$_2$—CH$_2$), 3.2 (br, 2H, CH$_2$—NH), 3.39 (br, 2H, CH$_2$—OH), 4.28 (q, 1H, —CH—CN), 4.38 (br, 1H, OH), 6.06 (br, 1H, 5-H-pyrimidine), 6.99 (d, 1H, 4-H—Ar—C—CN), 7.05 (br, 1H, CH$_2$NH), 7.09 (d, 3H, 3-H/5-H—Ar—NH), 7.32 (t, 1H, 5-H—Ar—C—CN), 7.39 (d, 1H, 6-H—Ar—C—CN), 7.48 (d, 2H, 2-H/6-H—Ar—NH), 7.63 (s, 1H, 2-H—Ar—C—CN), 8.12 (d, 1H, 6-H-pyrimidine), 8.73 (s, 1H, urea-NH), 8.82 (s, 1H, urea-NH).

Example 27

1-{4-[2-(2-Hydroxy-ethylamino)-pyrimidin-4-yloxy]-phenyl}-3-(3-trifluoromethyl-phenyl)-urea i) 1-[4-(2-methylsulfanyl-pyrimidin-4-yloxy)-phenyl]-3-(3-Trifluoromethyl-phenyl)-urea A solution of 41.7 g (219 mmol) 3-trifluoromethyl-phenyl isocyanate in 50 ml dichloromethane was added within 45 min. drop by drop at 5-10° C. to a solution of 51.0 g (219 mmol) 4-(2-Methylsulfanyl-pyrimidin-4-yloxy)-phenylamine and stirring continued for 5 h at 5° C. The reaction mixture was kept in a cooling room overnight at 4° C. The formed precipitate was isolated by cold filtration and washed thrice with 40 ml ice cold dichloromethane. After an additional washing with portions of isohexane (250 ml total) the product was dried at 40° C. in vacuum to give 73.4 g (80%) 1-[4-(2-methylsulfanyl-pyrimidin-4-yloxy)-phenyl]-3-(3-trifluoromethyl-phenyl)-urea.

$^1$H-NMR (400 Hz, [D$_6$]DMSO): δ=2.38 (s, 3H, SCH$_3$), 6.72 (d, 1H, 5-H-pyrimidine), 7.17 (d, 2H, 3-H/5-H—Ar—NH), 7.31 (d, 1H, 4-H—ArCF$_3$), 7.53 (t, 1H, 5-H—ArCF$_3$), 7.56 (d, 2H, 2-H/6-H—Ar—NH), 7.59 (d, 1H, 6-H—ArCF$_3$), 8.02 (d, 1H, 2-H—ArCF$_3$), 8.48 (d, 1H, 6-H-pyrimidine), 8.89 (s, 1H, urea-NH), 9.07 (s, 1H, urea-NH).

ii) 1-[4-(2-methanesulfonyl-pyrimidin-4-yloxy)-phenyl]-3-(3-Trifluoromethyl-phenyl)-urea 73.0 g (174 mmol) 1-[4-(2-methylsulfanyl-pyrimidin-4-yloxy)-phenyl]-3-(3-trifluoromethyl-phenyl)-urea were given to 400 ml ethyl acetate. A solution of 79.9 g (347 mmol) 77% 3-chloro-peroxybenzoic acid in 300 ml ethyl acetate was added drop by drop within 30 min. at −30° C. The reaction mixture was stirred for 1 h without cooling. After extraction with thrice 150 ml 2 M sodium carbonate solution and once with 150 ml water the organic phase was dried (sodium sulphate) and evaporated. The residue was leached with 80 ml ethyl acetate at 40° C. for 3 h. The precipitate was filtered and washed with 4×40 ml ice cold ethyl acetate. After drying in vacuum at 40° C. 51.8 g (66%) 3-(3-trifluoromethyl-phenyl)-1-[4-(2-methanesulfonyl-pyrimidin-4-yloxy)-phenyl]-3-(3-trifluoromethyl-phenyl)-urea were obtained.

$^1$H-NMR (400 Hz, [D$_6$]DMSO): δ=3.29 (s, 3H, SOCH$_3$), 7.27 (d, 2H, 3-H/5-H—Ar—NH), 7.31 (d, 1H, 4-H—ArCF$_3$), 7.34 (d, 1H, 5-H-pyrimidine), 7.52 (t, 1H, 5-H—ArCF$_3$), 7.59 (d, 2H, 2-H/6-H—Ar—NH), 7.60 (d, 1H, 6-H—ArCF$_3$), 8.03 (d, 1H, 2-H—ArCF$_3$), 8.88 (d, 1H, 6-H-pyrimidine), 8.94 (s, 1H, urea-NH), 9.09 (s, 1H, urea-NH).

iii) 1-{4-[2-(2-Hydroxy-ethylamino)-pyrimidin-4-yloxy]-phenyl}-3-(3-trifluoromethyl-phenyl)-urea A mixture of 1.13 g (2.50 mmol) 3-[4-(2-methanesulfonyl-pyrimidin-4-yloxy)-phenyl]-3-(3-trifluoromethyl-phenyl)-urea, 458 mg (7.5 mmol) 2-amino-ethanol and 10 ml ethyl acetate was stirred at r.t. for 24 h. The reaction mixture was diluted with ethyl acetate and extracted 4× with 5 ml water. The organic phase was dried (sodium sulphate) and evaporated. The oily residue was dissolved in 5 ml dichloromethane by gentle warming (30° C.). During stirring for 1 h at r.t. crystallization occurred. The precipitate was isolated washed thrice with 3 ml ice cold dichloromethane and dried in vacuum at 50° C. Yield 890 mg (80%) of the title compound.

MS: 434.00 (AP+), 432.01 (AP−).

$^1$H-NMR (400 Hz, [D$_6$]DMSO): δ=3.30 (br, 2H, CH$_2$—NH), 3.44 (br, 2H, CH$_2$—OH), 4.58 (br, 1H, OH), 6.09 (br, 1H, 5-H-pyrimidine), 6.94 (br, 1H, CH$_2$NH), 7.10 (d, 2H, 3-H/5-H—Ar—NH), 7.31 (d, 1H, 4-H—ArCF$_3$), 7.51 (d, 2H, 2-H/6-H—Ar—NH), 7.52 (t, 1H, 5-H—ArCF$_3$), 7.59 (d, 1H, 6-H—ArCF$_3$), 8.02 (s, 1H, 2-H—ArCF$_3$), 8.13 (d, 1H, 6-H-pyrimidine), 8.87 (s, 1H, urea-NH), 9.07 (s, 1H, urea-NH).

Example 28

1-(2,2-Difluoro-benzo[1,3]dioxol-5-yl)-3-{4-[2-(3-hydroxy-propylamino)-pyrimidin-4-yloxy]-phenyl}-urea 168 mg (1.04 mmol) 1,1'-Carbonyl-diimidazol (CDI) were given to a solution of 163 mg (0.941 mmol) 2,2-difluoro-5-amino-benzodioxole in 4.0 ml dichloromethane and stirred for 12 h. A solution of 245 mg (0.941 mmol) 3-[4-(4-Amino-phenoxy)-pyrimidin-2-ylamino]-propan-1-ol in 6 ml dichloromethane was added and the mixture stirred for 12 h at r.t. The reaction mixture was evaporated and the residue was purified by chromatography on silica gel (dichloromethane/ethanol 96:4). The obtained material was washed with dichloromethane, the precipitate was isolated by filtration and dried. Yield: 126 mg (29%) of the title compound.

MS: 460.1 (AP+), 458.05 (AP−).

$^1$H-NMR (400 Hz, [D$_6$]DMSO): δ=1.59 (br, 2H, CH$_2$—CH$_2$—CH$_2$), 3.23 (br, 2H, CH$_2$—NH), 3.40 (br, 2H, CH$_2$—OH), 4.37 (br, 1H, OH), 6.05 (br, 1H, 5-H-pyrimidine), 7.05 (br, 1H, CH$_2$NH), 7.09 (d, 2H, 3-H/5-H—Ar—NH), 7.10 (d, 1H, 6-H—ArOCF$_2$), 7.31 (d, 1H, 5-H—ArOCF$_2$), 7.47 (d, 2H, 2-H/6-H—Ar—NH), 7.66 (s, 1H, 2-H—ArOCF$_2$), 8.12 (d, 1H, 6-H-pyrimidine), 8.77 (s, 1H, urea-NH), 8.88 (s, 1H, urea-NH).

Example 29

1-(3,3-Dimethyl-2,3-dihydro-1H-indol-6-yl)-3-{4-[2-(3-hydroxy-propylamino)-pyrimidin-4-yloxy]-phenyl}-urea i) 6-(3-{4-[2-(3-Hydroxy-propylamino)-pyrimidin-4-yloxy]-phenyl}-ureido)-3,3-dimethyl-2,3-dihydro-indole-1-carboxylic acid phenyl ester 278 mg (1.71 mmol) 1,1'-Carbonyl-diimidazol (CDI) were given to a solution of 484 mg (1.63 mmol) 6-amino-3,3-dimethyl-2,3-dihydro-indole-1-carboxylic acid phenyl ester in 10 ml THF. A solution of 425 mg (1.63 mmol) 3-[4-(4-Amino-phenoxy)-pyrimidin-2-ylamino]-propan-1-ol in 10 ml THF was added within 15 min. and the mixture stirred for 12 h at r.t. The reaction mixture was evaporated and the residue was purified by chromatography on silica gel (dichloromethane/methanol 95:5). The obtained material was washed with dichloromethane/ether, the precipitate was isolated by filtration and dried. Yield: 540 mg (57%) of the title compound.

MS: 583.67 (ESI+).

ii) 1-(3,3-Dimethyl-2,3-dihydro-1H-indol-6-yl)-3-{4-[2-(3-hydroxy-propylamino)-pyrimidin-4-yloxy]-phenyl}-urea A mixture of 540 mg (927 mmol) 6-(3-{4-[2-(3-Hydroxy-propylamino)-pyrimidin-4-yloxy]-phenyl}-ureido)-3,3-dimethyl-2,3-dihydro-indole-1-carboxylic acid phenyl ester, 20 ml THF and 150 mg 10% Pd/C is hydrogenated at atmospheric pressure for 10 h. The catalyst is removed by filtration and the filtrate evaporated. The residue is purified by chromatography on silica (dichloromethane/methanol 95:5) and the obtained material (400 mg) stirred with dichloromethane for 1 h. the precipitate is isolated by filtration and washed with dichloromethane to give 150 mg (36%) of the title compound.

MS: 449.61 (AP+).

$^1$H-NMR (400 Hz, [D$_6$]DMSO): δ=1.20 (s, 6H, CH$_3$), 1.60 (br, 2H, CH$_2$—CH$_2$—CH$_2$), 3.16 (s, 2H, 2-H-indole), 3.23 (br, 2H, CH$_2$—NH), 3.39 (br, 2H, CH$_2$—OH), 4.37 (br, 1H, OH), 5.45 (s, 1H, NH-indole), 6.05 (br, 1H, 5-H-pyrimidine), 6.52 (d, 1H, 5-H-indole), 6.77 (s, 1H, 7-H-indole) 6.84 (d, 1H, 4-H-indole), 7.05 (br, 1H, CH$_2$NH), 7.07 (d, 2H, 3-H/5-H—Ar—NH), 7.45 (d, 2H, 2-H/6-H—Ar—NH), 8.11 (d, 1H, 6-H-pyrimidine), 8.35 (s, 1H, urea-NH), 8.57 (s, 1H, urea-NH).

Example 30

1-(4-Chloro-3-trifluoromethyl-phenyl)-3-{4-[2-((R)-2-hydroxy-1-methyl-ethylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.

MS: 482.1 (ESI+).

Example 31

1-(4-Chloro-3-trifluoromethyl-phenyl)-3-{4-[2-((R)-2-hydroxy-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.

MS: 482.1 (ESI+).

Example 32

1-(4-Chloro-3-trifluoromethyl-phenyl)-3-{4-[2-(2-hydroxy-1,1-dimethyl-ethylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.

MS: 496.1 (ESI+).

Example 33

1-(4-Chloro-3-trifluoromethyl-phenyl)-3-{4-[2-(2-hydroxy-1-hydroxymethyl-ethylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 498.1 (ESI+).

Example 34

1-(4-Chloro-3-trifluoromethyl-phenyl)-3-{4-[2-((S)-1-hydroxymethyl-2-methyl-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 510.1 (ESI+).

Example 35

1-(4-Chloro-3-trifluoromethyl-phenyl)-3-{4-[2-((1R,2R)-2-hydroxy-1-hydroxymethyl-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 512.1 (ESI+).

Example 36

1-(4-Chloro-3-trifluoromethyl-phenyl)-3-{4-[2-((R)-1-hydroxymethyl-2,2-dimethyl-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 524.1 (ESI+).

Example 37

1-(4-Chloro-3-trifluoromethyl-phenyl)-3-{4-[2-((S)-1-hydroxymethyl-2,2-dimethyl-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 524.1 (ESI+).

Example 38

1-(4-Chloro-3-trifluoromethyl-phenyl)-3-{4-[2-((1S,2S)-2-hydroxy-1-hydroxymethyl-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 512.1 (ESI+).

Example 39

1-(4-Chloro-3-trifluoromethyl-phenyl)-3-{4-[2-((R)-1-hydroxymethyl-2-methyl-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 510.1 (ESI+).

Example 40

1-(4-Chloro-3-trifluoromethyl-phenyl)-3-{4-[2-((S)-2-hydroxy-propylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 482.1 (ESI+).

Example 41

1-(4-Chloro-3-trifluoromethyl-phenyl)-3-{4-[2-((S)-2-hydroxy-1-methyl-ethylamino)-pyrimidin-4-yloxy]-phenyl}-urea The title compound was prepared in analogy to Example 10, step v) with subsequent purification by reversed phase HPLC, starting from 1-(4-Chloro-3-trifluoromethyl-phenyl)-3-[4-(2-methanesulfonyl-pyrimidin-4-yloxy)-phenyl]-urea and the appropriate amine.
MS: 482.1 (ESI+).

The invention claimed is:
1. A compound according to formula I,

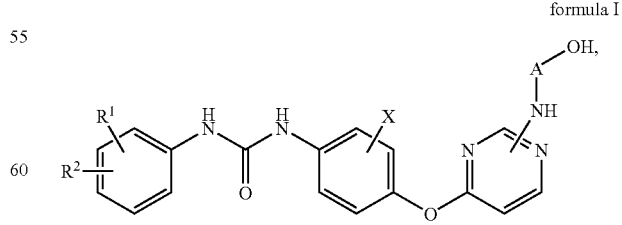

formula I wherein
$R^1$ is selected from the group consisting of: hydrogen, halogen, —$CF_3$, —$OCF_3$, alkyl, alkoxy, —$Si(CH_3)_3$, —$C_1$-$C_4$-alkylene-CN, —CN, and —$OCHF_2$;

R² is selected from the group consisting of: hydrogen, halogen, —CF₃, —OCF₃, alkyl, alkoxy, and —CN;
or alternatively R¹ and R² are adjacent and together with the carbon atom to which they are attached form a 5- or 6-membered heterocyclic ring, which is unsubstituted or substituted one to three times with halogen or alkyl;
X is selected from the group consisting of: hydrogen, fluorine, and chlorine;
A is $C_1$-$C_6$-alkylene, which is unsubstituted or substituted once or twice by hydroxy;
or a pharmaceutically acceptable salt thereof.

2. A compound according to claim 1, wherein
R¹ is selected from the group consisting of: hydrogen, CF₃, —OCF₃, alkyl, —Si(CH₃)₃, and or —$C_1$-$C_4$-alkylene-CN;
R² is selected from the group consisting of: hydrogen, halogen, and alkoxy;
or alternatively R¹ and R² are adjacent and together with the carbon atom to which they are attached form a 5- or 6-membered heterocyclic ring, which is unsubstituted or substituted one to two times with fluorine or alkyl;
X is selected from the group consisting of: hydrogen, fluorine, and chlorine;
A is $C_1$-$C_6$-alkylene, which is unsubstituted or substituted once or twice by hydroxy.

3. A compound according to formula I-a,

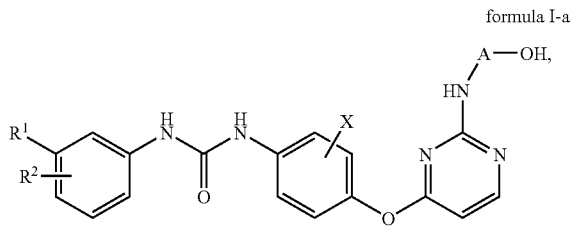

formula I-a wherein
R¹ is selected from the group consisting of: hydrogen, —CF₃, —OCF₃, alkyl, and —$C_1$-$C_4$-alkylene-CN;
R² is selected from the group consisting of: hydrogen, halogen, and alkoxy;
or alternatively R¹ and R² are adjacent and together with the carbon atom to which they are attached form a 5- or 6-membered heterocyclic ring, which is unsubstituted or substituted one to two times with fluorine or alkyl;
X is selected from the group consisting of: hydrogen, fluorine, and chlorine; and
A is $C_1$-$C_6$-alkylene, which is unsubstituted or substituted once or twice by hydroxy.

4. A compound according to formula I-b,

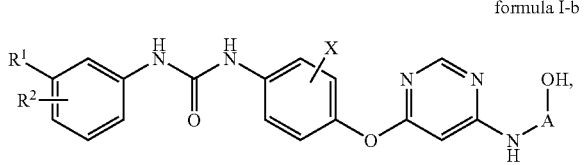

formula I-b wherein
R¹ is selected from the group consisting of: hydrogen, —CF₃, —OCF₃, alkyl, and —$C_1$-$C_4$-alkylene-CN;
R² is selected from the group consisting of: hydrogen, halogen, and alkoxy;
or alternatively R¹ and R² are adjacent and together with carbon atom to which they are attached form a 5- or 6-membered heterocyclic ring, which is unsubstituted or substituted one to two times with fluorine or alkyl,
X is selected from the group consisting of: hydrogen, fluorine, and chlorine; and
A is $C_1$-$C_6$-alkylene, which is unsubstituted or substituted once or twice by hydroxy.

5. A compound according to claim 1,
wherein
R¹ is hydrogen, CF₃, —OCF₃, and alkyl; and
R² is hydrogen, halogen, and alkoxy.

6. A compound according to claim 1, selected from the group consisting of:
1-{4-[2-(3-Hydroxy-propylamino)-pyrimidin-4-yloxy]-phenyl}-3-(4-trifluoromethoxy-phenyl)-urea;
1-(4-tert-Butyl-phenyl)-3-{4-[2-(3-hydroxy-propylamino)-pyrimidin-4-yloxy]-phenyl}-urea;
1-(4-Chloro-phenyl)-3-{4-[2-(3-hydroxy-propylamino)-pyrimidin-4-yloxy]-phenyl}-urea;
1-{4-[2-(3-Hydroxy-propylamino)-pyrimidin-4-yloxy]-phenyl}-3-phenyl-urea;
1-{4-[2-(3-Hydroxy-propylamino)-pyrimidin-4-yloxy]-phenyl}-3-(4-trimethylsilanyl-phenyl)-urea;
1-[4-(Cyano-dimethyl-methyl)-phenyl]-3-{4-[2-(3-hydroxy-propylamino)-pyrimidin-4-yloxy]-phenyl}-urea;
1-[3-(Cyano-dimethyl-methyl)-phenyl]-3-{4-[2-(3-hydroxy-propylamino)-pyrimidin-4-yloxy]-phenyl}-urea;
1-[3-(Cyano-methyl-methyl)-phenyl]-3-{4-[2-(3-hydroxy-propylamino)-pyrimidin-4-yloxy]-phenyl}-urea;
1-{3-Chloro-4-[2-(3-hydroxy-propylamino)-pyrimidin-4-yloxy]-phenyl}-3-(4-chloro-3-trifluoromethyl-phenyl)-urea;
1-{2-Chloro-4-[2-(3-hydroxy-propylamino)-pyrimidin-4-yloxy]-phenyl}-3-(4-chloro-3-trifluoromethyl-phenyl)-urea;
1-(4-Chloro-3-trifluoromethyl-phenyl)-3-{3-fluoro-4-[2-(3-hydroxy-propylamino)-pyrimidin-4-yloxy]-phenyl}-urea;
1-(4-Chloro-3-trifluoromethyl-phenyl)-3-{2-fluoro-4-[2-(3-hydroxy-propylamino)-pyrimidin-4-yloxy]-phenyl}-urea;
1-{4-[2-(3-Hydroxy-propylamino)-pyrimidin-4-yloxy]-phenyl}-3-(2-methoxy-5-trifluoromethyl-phenyl)-urea;
1-{4-[2-(3-Hydroxy-propylamino)-pyrimidin-4-yloxy]-phenyl}-3-(3-trifluoromethoxy-phenyl)-urea;
1-(3-tert-Butyl-phenyl)-3-{4-[2-(3-hydroxy-propylamino)-pyrimidin-4-yloxy]-phenyl}-urea;
1-{4-[2-(3-Hydroxy-propylamino)-pyrimidin-4-yloxy]-phenyl}-3-(3-trifluoromethyl-phenyl)-urea;
1-(2-Fluoro-5-trifluoromethyl-phenyl)-3-{4-[2-(3-hydroxy-propylamino)-pyrimidin-4-yloxy]-phenyl}-urea;
1-(4-Chloro-3-trifluoromethyl-phenyl)-3-{4-[2-(3-hydroxy-propylamino)-pyrimidin-4-yloxy]-phenyl}-urea;
1-(4-Chloro-3-trifluoromethyl-phenyl)-3-{4-[2-(4-hydroxy-butylamino)-pyrimidin-4-yloxy]-phenyl}-urea;
1-(4-Chloro-3-trifluoromethyl-phenyl)-3-{4-[2-(2-hydroxy-ethylamino)-pyrimidin-4-yloxy]-phenyl}-urea;
1-(4-Chloro-3-trifluoromethyl-phenyl)-3-{4-[2-(3-hydroxy-butylamino)-pyrimidin-4-yloxy]-phenyl}-urea;
1-(2-Chloro-5-trifluoromethyl-phenyl)-3-{4-[2-(3-hydroxy-propylamino)-pyrimidin-4-yloxy]-phenyl}-urea;
1-{4-[2-(2-Hydroxy-ethylamino)-pyrimidin-4-yloxy]-phenyl}-3-(3-trifluoromethyl-phenyl)-urea;
1-(4-Chloro-3-trifluoromethyl-phenyl)-3-{4-[2-((R)-2-hydroxy-1-methyl-ethylamino)-pyrimidin-4-yloxy]-phenyl}-urea;

1-(4-Chloro-3-trifluoromethyl-phenyl)-3-{4-[2-((R)-2-hydroxy-propylamino)-pyrimidin-4-yloxy]-phenyl}-urea;

1-(4-Chloro-3-trifluoromethyl-phenyl)-3-{4-[2-(2-hydroxy-1,1-dimethyl-ethylamino)-pyrimidin-4-yloxy]-phenyl}-urea;

1-(4-Chloro-3-trifluoromethyl-phenyl)-3-{4-[2-((S)-1-hydroxymethyl-2-methyl-propylamino)-pyrimidin-4-yloxy]-phenyl}-urea;

1-(4-Chloro-3-trifluoromethyl-phenyl)-3-{4-[2-((R)-1-hydroxymethyl-2,2-dimethyl-propylamino)-pyrimidin-4-yloxy]-phenyl}-urea;

1-(4-Chloro-3-trifluoromethyl-phenyl)-3-{4-[2-((S)-1-hydroxymethyl-2,2-dimethyl-propylamino)-pyrimidin-4-yloxy]-phenyl}-urea;

1-(4-Chloro-3-trifluoromethyl-phenyl)-3-{4-[2-((R)-1-hydroxymethyl-2-methyl-propylamino)-pyrimidin-4-yloxy]-phenyl}-urea;

1-(4-Chloro-3-trifluoromethyl-phenyl)-3-{4-[2-((S)-2-hydroxy-propylamino)-pyrimidin-4-yloxy]-phenyl}-urea;

1-(4-Chloro-3-trifluoromethyl-phenyl)-3-{4-[2-((S)-2-hydroxy-1-methyl-ethylamino)-pyrimidin-4-yloxy]-phenyl}-urea;

1-(4-Chloro-3-trifluoromethyl-phenyl)-3-{4-[2-(2-hydroxy-1-hydroxymethyl-ethylamino)-pyrimidin-4-yloxy]-phenyl}-urea;

1-(4-Chloro-3-trifluoromethyl-phenyl)-3-{4-[2-((1R,2R)-2-hydroxy-1-hydroxymethyl-propylamino)-pyrimidin-4-yloxy]-phenyl}-urea;

1-(4-Chloro-3-trifluoromethyl-phenyl)-3-{4-[2-((1 S,2S)-2-hydroxy-1-hydroxymethyl-propylamino)-pyrimidin-4-yloxy]-phenyl}-urea;

1-(2,2-Difluoro-benzo[1,3]dioxol-5-yl)-3-{4-[2-(3-hydroxy-propylamino)-pyrimidin-4-yloxy]-phenyl}-urea;

1-(3,3-Dimethyl-2,3-dihydro-1H-indol-6-yl)-3-{4-[2-(3-hydroxy-propylamino)-pyrimidin-4-yloxy]-phenyl}-urea;

1-{4-[6-(2-Hydroxy-ethylamino)-pyrimidin-4-yloxy]-phenyl}-3-(3-trifluoromethyl-phenyl)-urea;

1-{4-[6-(3-Hydroxy-propylamino)-pyrimidin-4-yloxy]-phenyl}-3-(3-trifluoromethyl-phenyl)-urea;

1-(4-Chloro-3-trifluoromethyl-phenyl)-3-{4-[6-(2-hydroxy-ethylamino)-pyrimidin-4-yloxy]-phenyl}-urea; and 1-(4-Chloro-3-trifluoromethyl-phenyl)-3-{4-[6-(3-hydroxy-propylamino)-pyrimidin-4-yloxy]-phenyl}-urea.

7. A process for the preparation of a compound according to claim 1, said process comprising:

reacting a compound of formula IV,

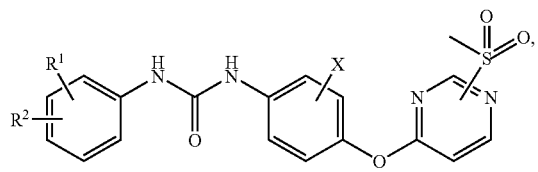

formula IV wherein $R^1$, $R^2$ and X have the significance given for formula I in claim 1, with a compound of formula IVa,

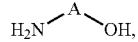

formula IVa wherein A has the significance given for formula I in claim 1, to give a compound of formula I,

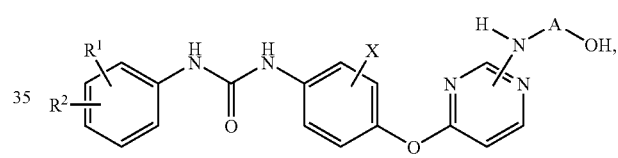

formula I wherein $R^1$, $R^2$, X and A have the significance given for formula I in claim 1.

8. A pharmaceutical composition comprising a compound according to claim 1 and a pharmaceutically acceptable carrier.

* * * * *